United States Patent
Crosby et al.

(10) Patent No.: US 7,074,194 B2
(45) Date of Patent: Jul. 11, 2006

(54) APPARATUS AND METHOD FOR RISK STRATIFICATION OF PATIENTS WITH CHEST PAIN OF SUSPECTED CARDIAC ORIGIN

(75) Inventors: Peter A. Crosby, Denver, CO (US); Deborah L. Morris, Boulder, CA (US); Mark M. Soane, Denver, CO (US)

(73) Assignee: Ischemia Technologies, Inc., Waltham, MA (US)

( * ) Notice: Subject to any disclaimer, the term of this patent is extended or adjusted under 35 U.S.C. 154(b) by 241 days.

(21) Appl. No.: 10/441,155

(22) Filed: May 19, 2003

(65) Prior Publication Data

US 2005/0004485 A1  Jan. 6, 2005

(51) Int. Cl.
*A61B 5/02* (2006.01)

(52) U.S. Cl. .................. 600/508; 600/513; 607/22

(58) Field of Classification Search .............. 607/6, 607/3, 22; 600/513, 508, 333
See application file for complete search history.

(56) References Cited

U.S. PATENT DOCUMENTS

| | | |
|---|---|---|
| 4,337,064 A | 6/1982 | Gindler et al. |
| 4,492,753 A | 1/1985 | Shell et al. |
| 4,546,776 A | 10/1985 | Bellin et al. |
| 4,568,647 A | 2/1986 | Sanford |
| 4,930,075 A | 5/1990 | Kortas |
| 5,173,422 A | 12/1992 | Knowles et al. |
| 5,173,431 A | 12/1992 | Pugia et al. |
| 5,182,214 A | 1/1993 | Kessler et al. |
| 5,223,392 A | 6/1993 | Cohen |
| 5,225,354 A | 7/1993 | Knowles et al. |
| 5,227,307 A | 7/1993 | Bar-Or et al. |
| 5,290,519 A | 3/1994 | Bar-Or et al. |
| 5,290,687 A | 3/1994 | Suslow et al. |
| 5,382,515 A | 1/1995 | Shah et al. |
| 5,515,859 A | 5/1996 | Paz |
| 5,532,136 A | 7/1996 | Carlsson et al. |
| 5,569,608 A | 10/1996 | Sommer |
| 5,604,105 A | 2/1997 | Jackowski |
| 5,620,856 A | 4/1997 | Carlson et al. |
| 5,670,627 A | 9/1997 | Johnson |
| 5,690,103 A | 11/1997 | Groth et al. |
| 5,710,008 A * | 1/1998 | Jackowski .................. 435/7.4 |
| 5,744,358 A | 4/1998 | Jackowski |
| 5,747,274 A | 5/1998 | Jackowski |

(Continued)

FOREIGN PATENT DOCUMENTS

EP          1 179 319 A1      2/2002

(Continued)

OTHER PUBLICATIONS

Cin et al (1996) Intl. J. Cardiol. 53(3):237.

(Continued)

*Primary Examiner*—Angela D. Sykes
*Assistant Examiner*—Roderick Bradford
(74) *Attorney, Agent, or Firm*—Swanson & Bratschun, LLC.

(57) ABSTRACT

The subject invention relates to the detection, diagnosis and risk stratification of clinical events such as acute coronary syndrome, in patients with signs and symptoms of suspected cardiac origin. In one embodiment, a clinical event in a patient is diagnosed by obtaining the patient's ECG, and at least one in vitro diagnostic assay, preferably an assay for a marker of ischemia, and optionally in vitro diagnostic assays for necrotic markers or other cardiac indicators, and combining the foregoing results in an algorithm to provide a diagnosis or a risk stratification of the clinical condition.

35 Claims, 10 Drawing Sheets

U.S. PATENT DOCUMENTS

| | | | |
|---|---|---|---|
| 6,033,364 | A | 3/2000 | Ohman et al. |
| 6,087,184 | A | 7/2000 | Magginetti et al. |
| 6,099,469 | A | 8/2000 | Armstrong et al. |
| 6,171,256 | B1 | 1/2001 | Joo et al. |
| 6,171,870 | B1 | 1/2001 | Freitag |
| 6,267,722 | B1 | 7/2001 | Anderson et al. |
| 6,268,223 | B1 | 7/2001 | Cornell-Bell et al. |
| 6,335,205 | B1 | 1/2002 | Bausback |
| 6,361,503 | B1 | 3/2002 | Starbin et al. |
| 6,394,952 | B1 * | 5/2002 | Anderson et al. ............ 600/300 |
| 6,410,341 | B1 | 6/2002 | Freitag et al. |
| 6,424,860 | B1 | 7/2002 | Karlsson et al. |
| 6,444,432 | B1 | 9/2002 | Kleinfeld |
| 6,461,875 | B1 | 10/2002 | Bar-Or et al. |
| 6,492,179 | B1 | 12/2002 | Bar-Or et al. |
| 6,507,753 | B1 | 1/2003 | Xue et al. |
| 2002/0133087 | A1 | 9/2002 | Bayer et al. |

FOREIGN PATENT DOCUMENTS

| | | |
|---|---|---|
| WO | WO 00/20454 | 4/2000 |
| WO | WO 00/20840 | 4/2000 |
| WO | WO01/088739 | 4/2002 |
| WO | WO 02/089656 | 4/2002 |
| WO | PCT/US02/39831 | 12/2002 |
| WO | WO02/096266 | 12/2002 |
| WO | WO 03/025571 | 3/2003 |
| WO | WO 2004/032711 | 4/2004 |

OTHER PUBLICATIONS

Belch et al. (1989) Free Radic. Biol. Med. 6(4):375-8.
Alpert, JS et al. (2000) J. Am. Coll. Card. 36:3.
Bar-Or et al. (2001) Am. Heart J. 141:985-991.
Bar-Or et al. (Jan. 2001) Eur. J. Biochem. 268:42-47.
Bar-Or et al. (1999) Ann. Emerg. Med. 34(4 Suppl.):s56.
Bar-Or et al. (2000) J. Emerg. Med. 19:4.
Biosite.com web page on Triage Cardiac Panel, printed Jun. 19, 2003.
Braunwald et al., Circulation (2002) 106:1893-1900.
Christenson et al. (2001) Clin. Chem. 47(3):464-470.
Hedges et al. (1996) Acad. Emerg. Med. 3:27-33.
Kleinfeld et al. (1996) Am. J. Cardiol. 78(12):1350-4.
Medscape, "Ruling Out Ischemia Saves Time and Money", Clinician Reviews 6(9):148, 150 (1996).
Morris D.L. (2001) Eur. Heart. J. Abs. Supp. 22:608.
Painter et al., 52$^{nd}$ Ann. Mtg. of Amer. Assn. Clin. Chemistry, Jul. 2000.
Pepine, C. (1994) J. Myocardial Ischemia 6(3):8.
Wu et al. (2001) Cardiovascular Toxicology 1(2):147-152.
Wu et al., Poster 37, Fourth Natl. Congress of Chest Pain Centers, Oct. 2000.
Wu et al., Third Ann. Joint Summit on Markers in Cardiology, 2000.
Bar-Or et al. (2002) Free Radical Biology & Medicine 32(2):197-199.
Veien et al. (1979) Contact Dermátitis 5:378.
Sadler et al. (1994) Eur. J. Biochem. 220(1):193.

* cited by examiner

APPARATUS AND METHOD FOR RISK STRATIFICATION OF PATIENTS WITH CHEST PAIN OF SUSPECTED CARDIAC ORIGIN

FIELD OF THE INVENTION

The subject invention relates to the detection, diagnosis and risk stratification of clinical events, such as acute coronary syndrome, in patients with signs and symptoms of suspected cardiac origin.

BACKGROUND OF THE INVENTION AND PRIOR ART

Each year in the United States, approximately eight million people present to a hospital emergency room (ER) with chest pain suggestive of cardiac origin (Storrow et al. (2000) Ann. Emerg. Med. 35:449), and even more present to their primary care physician. Acute Coronary Syndrome (ACS) presents as a constellation of symptoms such as chest pain, shortness of breath, inability to maintain physical exertion, sense of dread, pain or tingling on the left arm, and may also be accompanied by clinical signs such as altered electrocardiogram and elevation in biochemical markers of necrosis such as cardiac troponin. Chest pain of suspected cardiac origin is often referred to by its clinical description of angina pectoris. Chest pain is the number two reason for emergency room presentation, accounting for about eight percent of all patients.

The chest pain patient presents a diagnostic nightmare for the emergency room physician. On one hand, if the patient really is having a heart attack, early and rapid therapy is crucial to prevent more damage to the heart muscle, and missed diagnosis may result in poor consequences for the patient including death. On the other hand, if the patient is not having a heart attack and the physician keeps the patient in the hospital for a long time performing many diagnostic tests, the patients will consume precious health care resources that could be better spent on others. In fact, it is estimated that diagnosis of chest pain patients represents about $6 billion of wasted resources in the US alone.

The term "infarct" or "infarction" means a region of tissue which is dead and non-functional. For example, it is possible to have a brain infarct as a result of a stroke, or a bowel infarct as a result of severe bowel ischemia. A myocardial infarction (MI) is a region of dead heart muscle which is therefore unable to contribute to the pumping function of the heart. The term "heart attack" usually refers to an acute myocardial infarction or AMI, which is the emerging or developing MI, and is the end stage of ACS.

As a person ages, there is often a buildup of fatty plaque in the coronary arteries. The plaque is usually due to deposition of cholesterol from the blood, and consists of a soft core, with a harder membrane overlying it. At some time, a plaque may become unstable and rupture. A ruptured plaque will trigger a cascade of reactions in the blood, leading to formation of a clot or thrombus. The thrombus may be carried downstream in the coronary artery circulation, which becomes progressively narrower. Eventually, the thrombus will occlude a coronary artery, disrupting circulation and preventing blood supply to the cardiac muscle or myocardium.

Ischemia is the condition of imbalance between oxygen supply and demand. Ischemia can be transitory or continuous. In the case of myocardial ischemia, the oxygen supply is provided by the blood flow in the coronary arteries. The demand may depend on the physical exertion of the person. Thus, ischemia can result from increased demand with a limited supply (e.g.: as a result of increased stress with occluded coronary arteries), or from suddenly restricted supply, as may occur with plaque disruption and thrombus formation in a coronary artery. The first case is often referred to as stable angina. This word "stable" refers to the fact that the angina is reproducible because the restriction in supply is stable (and usually due to stable plaque), and the ischemia can be reversed by simply ceasing the activity. Unstable angina is chest pain which occurs when coronary artery flow is rapidly compromised due to disruption of a plaque (so called unstable plaque) and is inadequate to supply the oxygen demands of the heart during minimal activity. In this case, the ischemia cannot be stopped by ceasing activity, and it may deteriorate to something worse, such as acute myocardial infarction.

Once the blood supply to the myocardium is restricted, the myocardium becomes starved of oxygen, leading to ischemia. In the early stages, the tissue is reversibly ischemic, meaning that with resumption of blood supply the tissue will recover and return to normal function. After a while, the tissue becomes irreversibly ischemic, meaning that although the cells are still alive, if the blood supply is restored, the tissue is beyond salvation, and will inevitably die. Finally, the tissue dies (i.e., becomes necrosed), and forms part of the myocardial infarct. In fact, myocardial infarction is defined as "myocardial cell death due to prolonged ischemia."

The events which occur in an AMI are illustrated diagrammatically in FIG. 1. An occlusion of a coronary artery (1) results in reduced blood flow. Tissue becomes first reversibly ischemic, then irreversibly ischemic, and finally necrosed (dead). The tissue which has been ischemic for the longest time is that which dies first. Because much of the myocardial tissue is supplied via capillaries, regions furthest from the site of occlusion are the last to receive oxygenated blood, and therefore are ischemic for shorter time than the areas closer to the site of occlusion. Thus, there are several zones of conditions proceeding in the tissue downstream from the coronary artery occlusion. The zone furthest away is reversibly ischemic (2), progressing to irreversibly ischemic (3), then finally necrosed (4). Eventually the entire region of tissue becomes necrosed with no remaining ischemic tissue, and there is a complete infarct.

Patients presenting with chest pain may be having stable angina, unstable angina, AMI, non-ischemic cardiac problems such as congestive heart failure, or non-cardiac problems such a gastro esophageal reflux disease (GERD). The optimal therapy for each of these patient types and the urgency for therapy is quite different, hence rapid diagnosis and risk stratification has enormous clinical importance.

Until recently, the diagnosis of an MI was done retrospectively. The criteria established by the World Health Organization (WHO) defined MI as any two of the three characteristics of (a) typical symptoms (i.e., chest discomfort), (b) enzyme rise, and (c) typical ECG pattern involving the development of Q-waves (an indication of necrosed myocardium). With these criteria, which were established some years ago, the "enzyme rise" refers to the rise of serum levels of creatine kinase (CK) or its more cardiac specific isoform CK-MB. CK-MB is one of the molecules released from dead cardiac muscle cells and therefore is a serum marker of necrosis. As a heart muscle cell dies as a result of prolonged ischemia, the cell membrane ruptures, releasing the cytosolic contents into the extracellular fluid space, then into the lymphatic system, and from there it enters the bloodstream.

Since the WHO criteria were first promulgated, new biochemical markers of cardiac necrosis have been discovered and commercialized. (For a complete description of many of these markers, see Wu, A.H.B. (ed.) *Cardiac Markers*, Humana Press ISBN 0-89603-434-8, 1998). The most specific markers of cardiac necrosis so far developed are the cardiac troponins. These are proteins which are part of the contractile apparatus of myocardial cells. Two versions, cTnI and cTnT have been commercialized, and shown to be very specific for detection of even small amounts of myocardial damage. The cardiac troponins, similar to CK-MB, are released from dead cardiac muscle cells when the cell membrane ruptures, and are eventually detectable in the blood. Necrosis can certainly occur as a result of a prolonged myocardial ischemia, but can also result from myocardial cell damage from other causes such as infection, trauma, or congestive heart failure. Thus, the observation of an increase in cardiac markers of necrosis alone does not lead to a definitive diagnosis of myocardial infarction.

The cardiac markers described above are excellent markers of necrosis, but are not markers of ischemia. However, there is much confusion in the medical community and in the literature on this point, and it is not uncommon to see references to troponin, CK-MB and myoglobin (another marker of cardiac necrosis) being described as markers of cardiac ischemia. Although it is true that necrosis is always preceded by and is a consequence of ischemia, it is not true that ischemia always leads to necrosis. Therefore these necrosis markers are not necessarily markers of ischemia. For example, stable angina is cardiac ischemia as a result of exercise which will not necessarily lead to necrosis. If the person stops exertion, the demand will fall to the level which can be adequately supplied by the circulation, and the ischemia dissipates, and there is thus no elevation of markers of cardiac necrosis.

The American College of Cardiology (ACC) and the European Society of Cardiology (ESC) published a consensus document (Alpert, J. S. et al. (2000) J. Am. Coll. Card. 36:3) with a proposed redefinition of myocardial infarction. Part of the consensus document is a new definition of acute, evolving or emerging MI. The new definition is that either one of the following criteria satisfies the diagnosis for an acute, evolving or recent MI:

1. typical rise and gradual fall (troponin) or more rapid rise and fall (CK-MB) of biochemical markers of myocardial necrosis with at least one of the following:
   a. ischemic symptoms;
   b. development of pathologic Q-waves on the ECG;
   c. ECG changes indicative of ischemia (ST segment elevation or depression); or
2. coronary artery intervention (e.g., coronary angioplasty); or
3. pathologic findings of acute MI.

Implicit in this definition is the idea that an AMI includes both an ischemic component and a necrosis component. The problem is that although there are excellent biochemical markers of necrosis (i.e., troponin), there are no accepted biochemical markers of ischemia, and therefore reliance is made on clinical impressions combined with symptoms and changes in the ECG. The fact that troponin is not a marker of ischemia is highlighted in the consensus document which states "these biomarkers reflect myocardial damage but do not indicate its mechanism. Thus an elevated value in the absence of clinical evidence of ischemia should prompt a search for other causes of cardiac damage, such as myocarditis."

The problem is that cardiac ischemia is extremely difficult to diagnose. The National Heart Lung and Blood Institute (NHLBI) of the U.S. National Institutes of Health (NIH) created a National Heart Attack Alert Program (NHAAP) in the early 1990s. In 1997, a working group of the NHAAP published an evaluation of all technologies available at the time for identifying acute cardiac ischemia in the emergency department (Selker, H. P. et al. (1997) A Report from the National Heart Attack Alert Program (NHAAP) Coordinating Committee Blackwell Science ISBN 0-632-04304-0). The key reason for this report was that new technologies for reperfusion (in particular percutaneous transluminal coronary angioplasty or PTCA, and a whole class of thrombolytic drug therapies such as TPA (tissue plasminogen activator) and streptokinase) had shown that dramatic improvements in mortality and morbidity were related to the interval between the onset of chest pain and the start of therapy. This is clearly because the earlier therapy can be applied, the more of the myocardial tissue is still reversibly ischemic instead of necrosed, and therefore there is higher likelihood that it will recover if blood supply is restored. Obviously, the key to reducing the time to therapy is to improve the performance of diagnostic tests in the emergency department (ED) such that the diagnosis can be made earlier while reversible ischemia is still present. In fact, the introduction of the NHAAP book states that "identifying only AMI would miss a large number of ED patients at significant and immediate cardiac risk."

The standard of care and the most widely accepted tool for diagnosis of ACS in the ED is the standard twelve lead electrocardiogram (ECG or EKG). Changes such as ST Segment Elevation are indicative of injury to the myocardium, and lead to a diagnosis of MI. Changes such as ST Segment depression are indicative of ischemia. The ECG is also used to diagnose and classify arrhythmias such as atrial fibrillation and ventricular tachycardia. A patient with an arrhythmia such as Left Bundle Branch Block (LBBB) obscured features on the ECG and makes the ECG uninterpretable for ACS.

The ECG suffers from imperfect sensitivity and specificity for acute cardiac ischemia, and when interpreted using stringent criteria for AMI, sensitivity drops to 50% or below. Other tools which have been investigated but not yet well accepted include variations on the ECG or algorithms involving the ECG, cardiac markers such as CK-MB and TnI, radionuclide myocardial perfusion imaging (MPI) using $^{99}$Tc sestamibi and thallium, ECG exercise stress test, and ultrasound echocardiography. None of these has been shown to have consistently reliable sensitivity and specificity to the point where it has been accepted as standard of care. Furthermore, some technologies such as MPI, while offering relatively good accuracy, are expensive and have limited availability.

There have been several attempts to develop a device and/or algorithms for diagnosing AMI in chest pain patients using biochemical markers (see, for example, Jackowski, G., U.S. Pat. No. 5,710,008 (1998)). The '008 patent describes a method and a device for using a combination of at least three biochemical markers in conjunction with an algorithm for diagnosis of AMI. Cardiac Troponin has been accepted as the "gold standard" biochemical marker for diagnosis of acute myocardial infarction. The clinical performance of Troponin I has been reported by many publications, and by many manufacturers of troponin assays.

Although troponin is a very specific marker for cardiac necrosis, its clinical utility, especially in the early period following onset of chest pain (i.e., immediately after the coronary artery occlusion leading to ischemia) is limited by the slow kinetics of the marker itself, and the fact that it is a marker for necrosis, not ischemia, and therefore released late in the clinical sequence. In other words, the clinical sensitivity of troponin for detection of AMI approaches 100% provided sufficient time has elapsed. However, the clinical sensitivity of troponin for detection of AMI (or ACS) is less than 20% at presentation of a patient within 2 hours of the onset of chest pain (Mair et al. (1995) Clin. Chem. 41:1266; Antman et al. (1995) JAMA 273:1279). This is important because the median time for presentation to a hospital emergency room after onset of chest pain is about two hours in patients who will be subsequently diagnosed as having AMI (Goff et al. (1999) Am. Heart J. 138:1046).

Attempts to obtain better diagnosis of AMI using combinations of results from biochemical markers of necrosis have been described. For example, Shah et al., U.S. Pat. No. 5,382,515 (1995), describe an algorithm using sequential closely spaced measurements of different isoforms of creatine kinase to determine both the presence and the time of an AMI. The concept was expanded by Groth, T. et al., U.S. Pat. No. 5,690,103 (1997), who describe the use of an algorithm implemented by a neural network whose inputs are several closely spaced measurements of several markers released from necrotic tissue (CK-MB and troponin). Although this method may be beneficial in that it is still better than measurement of a single necrosis marker, or multiple necrosis markers at a single time, it is still not possible to make the determination until at least three hours have passed, and does not work for detection of ischemia since only necrosis markers are used.

A similar approach (although without a neural network) was proposed by Armstrong et al. (U.S. Pat. No. 6,099,469 (2000)), although in this case the algorithm is designed to run on the computer embedded in an automated laboratory analyzer, and suggests which test should be performed next. Again, the Armstrong invention suffers from the limitation that it uses only markers of necrosis, and requires multiple sequential measurements to achieve adequate performance.

Ohman et al. (U.S. Pat. No. 6,033,364 (2000)) described algorithms using combinations of existing markers of necrosis which have also been used to assess reperfusion after thrombolytic therapy. In this invention, an algorithm using sequential measurements of a necrosis marker (CK-MB) and a model based on the rise and fall kinetics of CK-MB can determine when therapy has allowed restoration of coronary artery flow and therefore arrested the growth of infarcted tissue and hence release of further markers of necrosis.

Partly as a result of the difficulty of obtaining a firm diagnosis in chest pain patients, there has been a growing emphasis in clinical medicine in recent years to focus more on risk stratification than a hard diagnostic endpoint. To meet these clinical practice guidelines, emergency physicians need diagnostic tools and procedures that can help identify high risk ACS patients in less than 30 minutes. The concept of a "Chest Pain Evaluation Unit" (CPEU) has gained rapid acceptance in the emergency medicine field. The basic concept is rapid risk stratification based on ECG, clinical presentation, and often troponin, in a hierarchy. High risk patients may receive more aggressive diagnostic testing (e.g.: cardiac catheterization) and therapy (e.g.; anti-coagulant drugs), whereas low risk patients may be relegated to watchful waiting and eventual discharge. Patients who can not be adequately risk stratified at presentation are subjected to serial testing, and often provocative testing such as stress ECG. With currently available tools combining ECG and troponin, only about 25% of patients can be reliably risk stratified at presentation, and the remainder will spend many hours with serial testing and watchful waiting before receiving therapy or being discharged.

One of the problems with early risk stratification of chest pain patients has been the problem of obtaining rapid assessment of biochemical markers such as troponin when the instruments are in a central laboratory, and may not be configured for "stat" utilization. As a result, there has been a growing interest in Point of Care (POC) Testing, often with dedicated instruments placed in the emergency room or near the patient to perform a limited number of diagnostic tests, but to give the results in a short period of time. For example, Anderson et al in U.S. Pat. No. 6,394,952 and U.S. Pat. No. 6,267,722 "Point of Care Diagnostic Systems" describe an apparatus for performing rapid testing and turning the results into diagnostic or risk assessment information.

Interpretation of an electrocardiogram is fraught with error, particularly by physicians who do not perform this task often and routinely. To help solve this problem, electrocardiographic machines have been developed which perform automatic analysis on the ECG, for example to look at deviations of the ECG ST segment to determine if ischemia is present or absent. See U.S. Pat. No. 4,546,776 "Portable EKG Monitoring Device for ST Deviation" for an early example of this technology. Many algorithms have been invented for improving the performance of equipment to detect ST segment changes indicative of cardiac ischemia— see for example U.S. Pat. No. 6,507,753 (2003) "Method and Apparatus to Detect Acute Cardiac Syndromes in Specified Groups of Patients using ECG", and U.S. Pat. No. 4,930,075 (1990) "Technique to Evaluate Myocardial Ischemia from ECG Parameters". Alternative parameters in the ECG have been evaluated as a detector for ischemia, including interval data—see for example U.S. Pat. No. 6,361,503 (2002) "Method and System for Evaluating Cardiac Ischemia". Because of the relatively poor performance of ECG as a signal source for diagnosis of ischemia, there have been attempts to allow the user to "trade off" sensitivity and specificity in the way the algorithms are performed, see for example U.S. Pat. No. 6,171,256 B1 (2001) "Method and Apparatus for Detecting a Condition Associated with Acute Cardiac Ischemia".

This shift in emphasis from hard diagnosis to risk stratification which has been seen in the recent use of biochemical markers has also had an impact on the world of electrocardiography. Inventions have been directed towards estimating the probability that a patient has cardiac ischemia as opposed to merely providing a "yes" or "no" diagnostic answer. For example, in US Patent Application US2002/0133087A1 (2002), "Patient Monitor for Determining a Probability that a Patient has Acute Cardiac Ischemia", the inventors use continuously monitored and analyzed ECG signals to provide a numerical probability of acute cardiac ischemia for a patient in an emergency department. A similar objective is targeted in the invention described in European Patent Application EP. 1.179.319.A1 (2001) "Method and Apparatus to Detect Acute Cardiac Syndromes in Specified Groups of Patients using ECG".

There would be an advantage to providing diagnosis of ACS before a patient presents to an emergency room, for example in an ambulance or in the physician's office. Some inventions have been directed towards improving the performance of ECG analysis in a telemedicine environment— see for example U.S. Pat. No. 6,424,860 "Myocardial Ischemia and Infarction Analysis and Monitoring Method and Apparatus." There have also been attempts to detect ischemia using an implantable device (see U.S. Pat. No. 6,128,526 "Method for Ischemia Detection and Apparatus Using Same").

However, the object of the inventions described above is to improve the analytical performance of equipment where the fundamental signal source—ECG—is flawed or inadequate. Thus there is a need to provide more and better tools for emergency medicine physicians, and others, to make more reliable assessment of a patient's risk of cardiac ischemia at presentation, both using existing sources of diagnostic information and, more importantly, combinations of new and existing sources of information.

SUMMARY OF THE INVENTION

It is an objective of the present invention to use one or more biochemical markers in conjunction with the electrocardiogram to perform a diagnosis of clinical conditions such as ACS, or risk stratification of patients presenting with suspected ACS. Furthermore, it is an objective of the present invention to use a biochemical marker of ischemia in conjunction with the ECG to perform the diagnosis or risk stratification of patients presenting with chest pain suspected to be cardiac ischemia. It is a further object of the present invention to use a biochemical marker of ischemia, in conjunction with a biochemical marker of myocardial necrosis, to perform the diagnosis or risk stratification of patients presenting with chest pain suspected to be cardiac ischemia. Finally, it is an object of the present invention to provide for a method whereby the algorithm by which the results of the ECG tests and the in vitro diagnostic assays are combined is continuously improved as a result of learning from prior experience, by accessing the results of previous tests and comparing the results with the clinical diagnosis or outcome of the patient.

In its broadest aspect, the subject invention comprises a method for diagnosing a clinical event occurring in a patient by obtaining from the patient at least one sample of a substance stream from the patient (e.g.: from the bloodstream); conducting a first in vitro diagnostic assay and optionally additional in vitro diagnostic assays on the sample; performing an electrocardiographic test on the patient; and combining the results of the foregoing tests using an algorithm to provide, for example, a positive or negative diagnosis of the clinical event, or a risk stratification or assessment of the risk of a clinical condition. Note that the sequence of events of performing the ECG and in vitro diagnostic tests is unimportant, and they can be performed in the order described above or any other order, or simultaneously. An "algorithm" as used herein refers to the steps involved in making a diagnosis or assessment of the risk (or probability) of the occurrence of a clinical condition utilizing the results of one or more of the ECG and the diagnostic tests. As used herein, "risk stratification" refers to an estimation of the probability (risk) that the patient has the clinical condition at the time the sample is taken; for purposes of the subject application, this term does not refer to predictions of the risk of future episodes of the clinical condition for the patient. The invention also includes an apparatus to achieve the described method, which in simple terms consists of a housing containing an electrocardiograph means and an apparatus for performing an in vitro diagnostic test on a patient sample, and may also include computing and processing means within the machine for performing the calculations of the algorithm.

The substance stream refers to any flowing body tissue or fluid including but not limited to urine, saliva, tears, semen, mucus, feces, blood, lymph, serum, plasma and expired breath.

The clinical condition can be, for example, an acute myocardial infarction (AMI), acute cardiac ischemia (ACI), Acute Coronary Syndrome (ACS), or unstable angina (UA). If the clinical condition is ACS, UA or ACI, the assay for a molecule that is present in the stream and which is modified by the clinical event, can be an assay for ischemia modified albumin (IMA). The patient sample can be blood, serum or plasma and the assay for ischemia modified albumin can be, for example, the Albumin Cobalt Binding (ACB®) Test or an immunoassay specific for ischemia modified albumin, i.e., using antibodies directed to the altered N-terminus of albumin, a metal affinity assay for IMA, or an electrochemical or optical test for IMA. Some of these methods are described in U.S. Pat. Nos. 5,290,519, 5,227,307, 6,492,179, and 6,461,875, and co-pending patent applications which are hereby incorporated by reference: U.S. Ser. No. 10/304,610, U.S. Ser. No. 09/849,956, U.S. Ser. No. 10/319,263, U.S. Ser. No. 09/846,411 and PCT/US02/16860.

The subject invention also includes a method for ruling out a diagnosis of a clinical condition such as ACS, ACI or UA by obtaining a sample of a patient's blood, serum or plasma, conducting at least one in vitro assay for a marker of cardiac ischemia and/or a marker of cardiac necrosis, and combining the results of the assay(s) with the results of the ECG analysis using an algorithm to provide a negative diagnosis or assessment of low risk. A negative diagnosis may be made where all ischemia marker tests and all necrosis marker tests are negative, or where the majority of both the ischemic marker tests and necrosis marker tests are negative, when the ECG is either "normal" or "non-diagnostic". As is discussed herein, the subject method can have the advantage of a high negative predictive value (NPV), making it useful in ruling-out the occurrence of a ACS or AMI. Ruling-out AMI or ACS relatively early after patient presentation at an emergency room can lead to early patient release and conservation of medical resources.

DETAILED DESCRIPTION OF THE INVENTION

Figure 1:
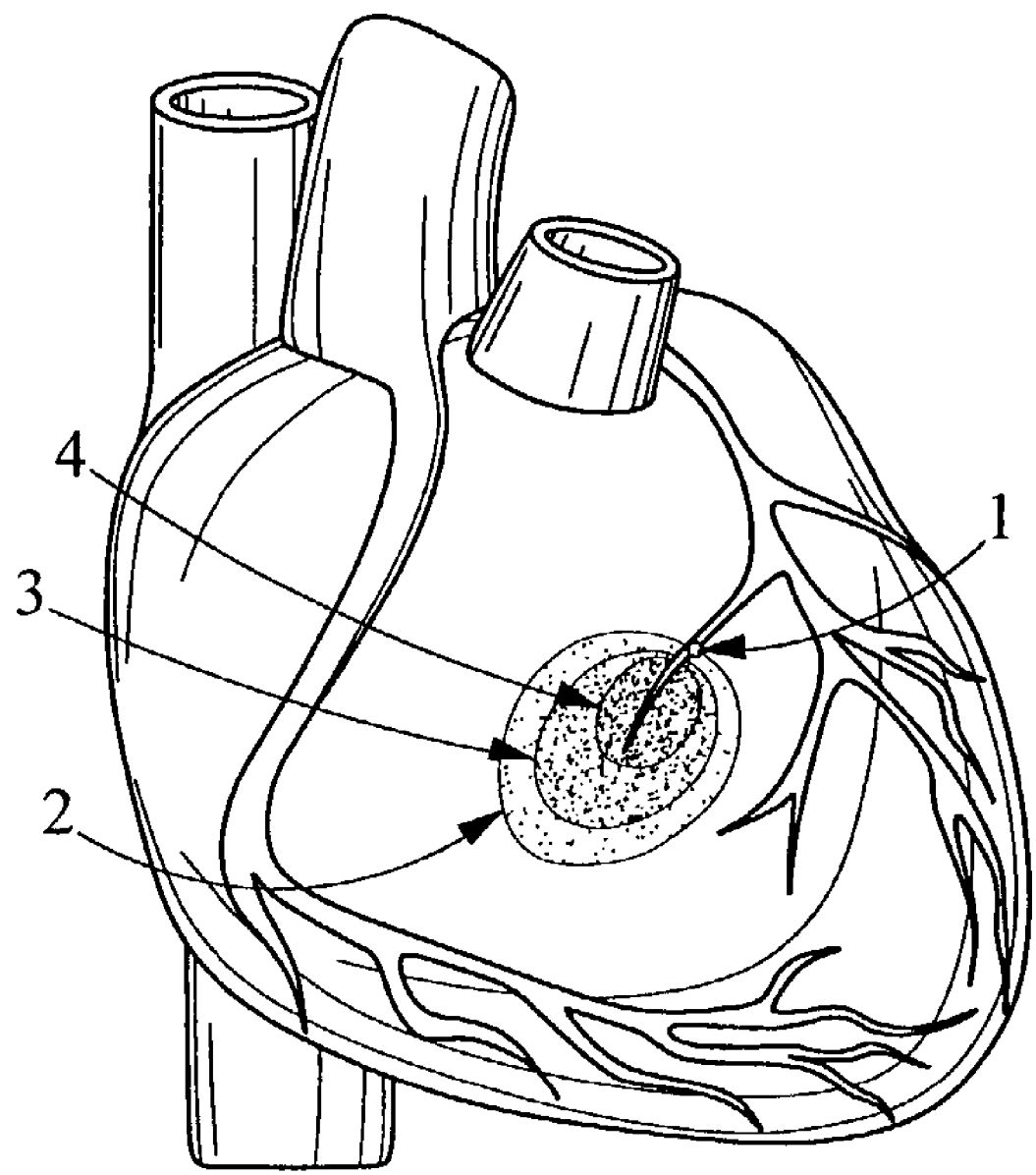
FIG. 1 is a diagrammatic illustration of the zones of reversibly ischemic, irreversibly ischemic, and necrotic tissue a short time after a coronary artery occlusion.

It has been found that the N-terminus of human serum albumin can be modified by exposure to ischemic tissue in such a way that it is less capable of binding certain metals, in particular cobalt. The detection of such ischemia modified albumin (IMA™) is embodied in the Albumin Cobalt Binding Test (ACB™ Test) developed by Ischemia Technologies, Inc., Denver, Colo. The measurement of modified metal binding ability of serum proteins (including albumin) for detection of ischemia was first described in BarOr, D. et al. (see (1993) U.S. Pat. No. 5,227,307, *Test for the Rapid Evaluation of Ischemic State*, and BarOr, D. et al. and (1994) U.S. Pat. No. 5,290,519, *Test for the Rapid Evaluation of Ischemic States and Kit*). Further developments relating to diagnosis of ischemia have been described in U.S. Pat. Nos. 6,492,179, and 6,461,875, all of which are hereby incorporated in their entireties by reference. Preliminary results of experiments to confirm the mechanism of IMA have also been published (BarOr D, Curtis G, Rao N, Bampos N, Lau E. *Characterization of the Co2+ and Ni2+ Binding Amino-Acid Residues of the N-terminus of Human Albumin*. Eur. J. Biochem. 200; 268, 42–47).

There is a fundamental difference between conventional markers of necrosis such as troponin, myoglobin and CK-MB (for example, as described by Jackowski, et al., supra) and the use of ischemia modified albumin. In the former case, biochemical markers of necrosis are molecules available in the bloodstream some time after the cytosolic contents of a cell are released as a result of rupture of the cell membrane from necrosis. The molecules are released first into the extracellular space, from there to the lymphatic system, and thence drain into the bloodstream. In the case of IMA, albumin is circulating in blood, and is rapidly modified as a result of exposure to ischemic tissue. Therefore, there is no requirement for the cell membranes to rupture, nor is there a long time delay between the event leading to ischemia and the time the biochemical marker can be detected in the bloodstream. The ACB Test has been demonstrated to detect the rapid rise in IMA following a transient ischemic event, caused by percutaneous transluminal coronary angioplasty (PTCA) (BarOr D, Winkler J, VanBenthuysen K, Harris L, Lau E, Hetzel F. "*Reduced albumin-cobalt binding with transient myocardial ischemia after elective percutaneous transluminal coronary angioplasty: A preliminary comparison to creatine kinase-MB, myoglobin and troponin I*" Am Heart J, 2001; 141:985–991). PTCA is a procedure during which a catheter is threaded into a coronary artery via radiographic guidance to the location of a coronary artery occlusion. The catheter has a long thin balloon at its tip. When in position, the balloon is inflated, pushing the plaque up against the wall of the artery, thereby increasing the size of the lumen, and restoring flow upon balloon deflation. The PTCA procedure is well accepted in clinical practice.

At the time of balloon inflation (typically 30 seconds to two or three minutes), there is no coronary artery flow. The absence of flow therefore induces temporary ischemia downstream from the site of balloon inflation. However, this short duration of ischemia does not induce the changes seen as a result of long duration ischemia, such as cell necrosis.

Further studies showing the utility of the ACB Test as a diagnostic tool are described in BarOr D, Lau E, Winkler J. "*A Novel Assay for Cobalt-Albumin Binding and its Potential as a Marker for Myocardial Ischemia—a Preliminary Report*" J Emerg Med 2000; 19:4.; Wu AHB, Morris D L, Fletcher D R, Apple F S, Christenson R H, Painter P C. "*Analysis of the Albumin Cobalt Binding (ACB™) Test as an Adjunct to Cardiac Troponin for the Early Detection of Acute Myocardial Infarction*" Cardiovascular Toxicology, 2001; 1:2, 147–152.; and Christenson R L, Duh S H, Sanhai W R, Wu A H B, Holtman V, Painter P, Branham E, Apple F S, Murakami M A, Morris D L. "*Characteristics of an Albumin Cobalt Binding Test for Assessment of Acute Coronary Syndrome Patients: A Multicenter Study*" Clinical Chemistry 2001; 47:3, 464–470.

As discussed above, one embodiment of the subject invention includes an improved method for risk stratification of the suspected ACS patient by conducting at least one test for a marker of ischemia and optionally another in vitro diagnostic test, in conjunction with measuring the ECG, and combining all the results in an algorithm. Preferably, the in vitro diagnostic test should be for a necrosis marker. Preferably, the test for the ischemic marker is a test for IMA such as the ACB Test, and the necrosis marker test is a troponin assay. Alternatively, the necrosis markers can be CK-MB or myoglobin or other necrotic markers known in the art, such as those described in Wu, A. H. B. (1998), supra.

A further embodiment of the present invention is where the ECG is combined with more than one test for the ischemia marker, such that each test provides additional information about the ischemia. Another possible marker of ischemia is Free Fatty Acids or FFA (see Kleinfeld A M, Prothro D, Brown D L, Davis R C, Richieri G V, DeMaria A *Increases in Serum Unbound Free Fatty Acid Levels Following Coronary Angioplasty*. Am. J. Cardiol. 1996 Dec. 15; 78(12):1350–4), and thus the ECG can be combined with FFA, with IMA, or with both.

A further embodiment of the present invention is where the ECG is combined with the ischemic marker result and additionally with more than one test for myocardial necrosis marker, including troponin, CK-MB, or myoglobin.

A further embodiment of the present invention is where the ECG is combined with the ischemic marker assay result, plus other markers useful in cardiology (i.e.: not markers of ischemia and not markers of necrosis) such as a marker of inflammation like C-Reactive Protein (CRP), or a marker of myocardial muscle load such a B type natriuretic peptide (BNP) or associated molecules such as N-terminal pro-BNP.

The relationship between the ECG and troponin for diagnosis has been defined in guidelines published by the American Heart Association and the American College of Cardiology (Braunwald et al., "*Management Of Patients With Unstable Angina And Non-St-Segment Elevation Myocardial Infarction Update*" ACC/AHA 2002 Guideline Update for the Management of Patients With Unstable Angina and Non-ST-Segment Elevation Myocardial Infarction, A Report of the American College of Cardiology/American Heart Association Task Force on Practice Guidelines (Committee on the Management of Patients With Unstable Angina) Circulation, October 2002; 106:1893–1900)). The guidelines state that after clinical signs and symptoms, the ECG is used as the first diagnostic tool. If the ECG is normal or not helpful, then markers of necrosis such as troponin are the next diagnostic tool.

However, it is believed that there are no prior art publications on the use of the combination of ECG and a biochemical marker of ischemia, since prior to the advent of Ischemia Modified Albumin there has not been a biochemical marker of ischemia available.

Furthermore, the published guidelines refer to the use of ECG and troponin for ruling in a patient with suspected ACS (i.e.: making a positive diagnosis). The ECG and troponin can not be used for early rule out (i.e.: making a negative diagnosis) because the sensitivity of ECG and troponin alone or in combination is too low to yield a clinically acceptable negative predictive value. The primary reason for this is that troponin is a slow rising marker (first detectable within 6 hours of the onset of chest pain, and peaks within 24 hours) such that the guidelines indicate that there is no point in taking a troponin measurement earlier than 6 hours from the onset of chest pain. On the other hand, IMA is a rapidly rising marker with high sensitivity, so therefore it can be used for both rule in and rule out—not possible with the present technology.

In the present invention, the risk of the patient is computed according to an algorithm and indicated by considering the ECG and the results from a test for at least one marker of ischemia and optionally at least one marker of necrosis (e.g.: troponin).

Figure 6:
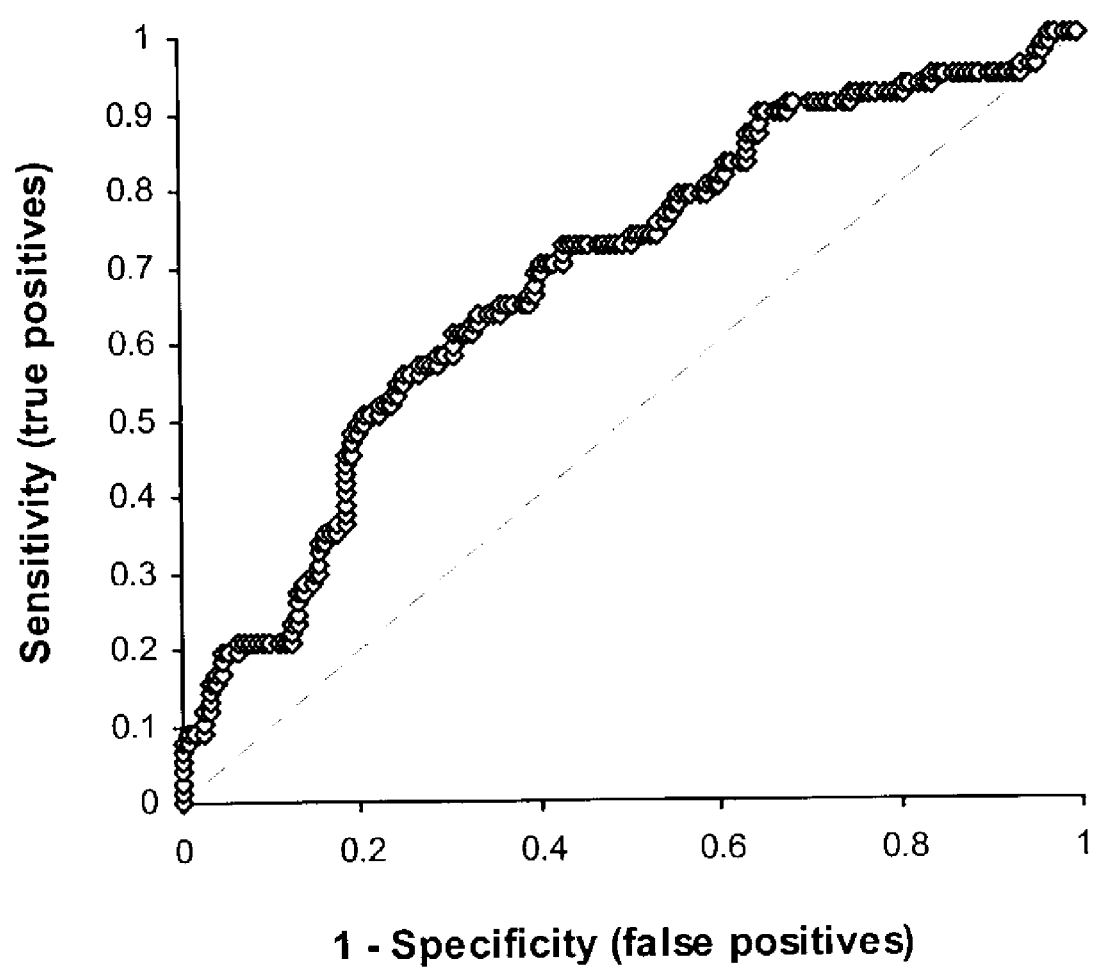
FIG. 6 is a graph of the Receiver Operating Characteristics (ROC) curve for IMA for detection of ACS from Study 1.

For example, the algorithm may comprise making a positive diagnosis for ACS if the ECG is diagnostic for ACS (e.g.: ST segment elevation). If the ECG is normal or non diagnostic (e.g.: there is an arrhythmia), then the patient is at highest risk if at least one of the tests for necrosis is positive (regardless of the value of the test for the marker(s) of ischemia), and is at higher (but not highest) risk if all marker(s) of necrosis are normal and at least one of the tests for ischemia is positive, and is at lowest risk when all of the tests for necrosis and all of the tests for ischemia are negative. The algorithm may also take into account the quantitative value of the ischemia marker or other in vitro diagnostic test to provide an estimate of the patient's probability of having the clinical condition. FIG. 6 (from Example 1, described below), shows the probability of a patient having ACS as a function of the values of the cardiac Troponin T test and the ACB Test to measure IMA. Therefore, one embodiment of the present invention is an algorithm which takes the output of the ECG analysis and if it is either normal or non-diagnostic for ischemia, then the values of IMA and troponin together are used to compute a probability of the patient having ACS.

The algorithm may also take into account the probability that a patient has the clinical condition as determined by the analysis of the ECG alone (e.g.: using the invention of US2002/0133087A1 supra), and combining this probability with the probabilities determined by the results of the in vitro diagnostic tests, for example by utilizing Bayes' theorem.

An example of an algorithm is shown in Table 1, where binary (i.e.: positive or negative) results of the tests are used (although of course a similar algorithm which uses quantitative results of each of the tests is also applicable). This algorithm is hierarchical, and ordered in that the highest risk conditions are at the top of the table, and risk decreases going down that table. That is, if the ECG provides definite diagnostic information (e.g.: ST Segment Elevation), then the diagnosis is clear and no other tests are necessary. If the ECG is non-diagnostic or normal, and troponin is elevated, then the diagnosis is by definition Non-ST Elevation Myocardial Infarction (NSTEMI), and no other tests are required to make the diagnosis. If the ECG is non-diagnostic or normal, and troponin is negative (i.e.: below the diagnostic cutoff), and IMA is elevated, then the patient probably has ACS. If the ECG is non-diagnostic or normal, and troponin and IMA are not elevated, then the diagnosis is probably non ischemic chest pain.

TABLE 1

| ECG | IMA | Troponin | Diagnosis |
| --- | --- | --- | --- |
| ST Segment elevation | +/− | +/− | ST Segment Elevation Myocardial Infarction |
| ST Segment depression | +/− | +/− | ST Segment depression ACS |
| Normal or non-diagnostic | +/− | + | Non-ST Elevation Myocardial Infarction |
| Normal or non-diagnostic | + | − | ACS (probable ACI or UA) |
| Normal or non-diagnostic | − | − | Non-ischemic chest pain |

The algorithm to be used can incorporate additional parameters such as the patient's physical characteristics, family history, or nature and duration of chest pain. The algorithm can be extended to incorporate other markers of ischemia, necrosis, or others (e.g.: BNP or CRP).

Figure 4:
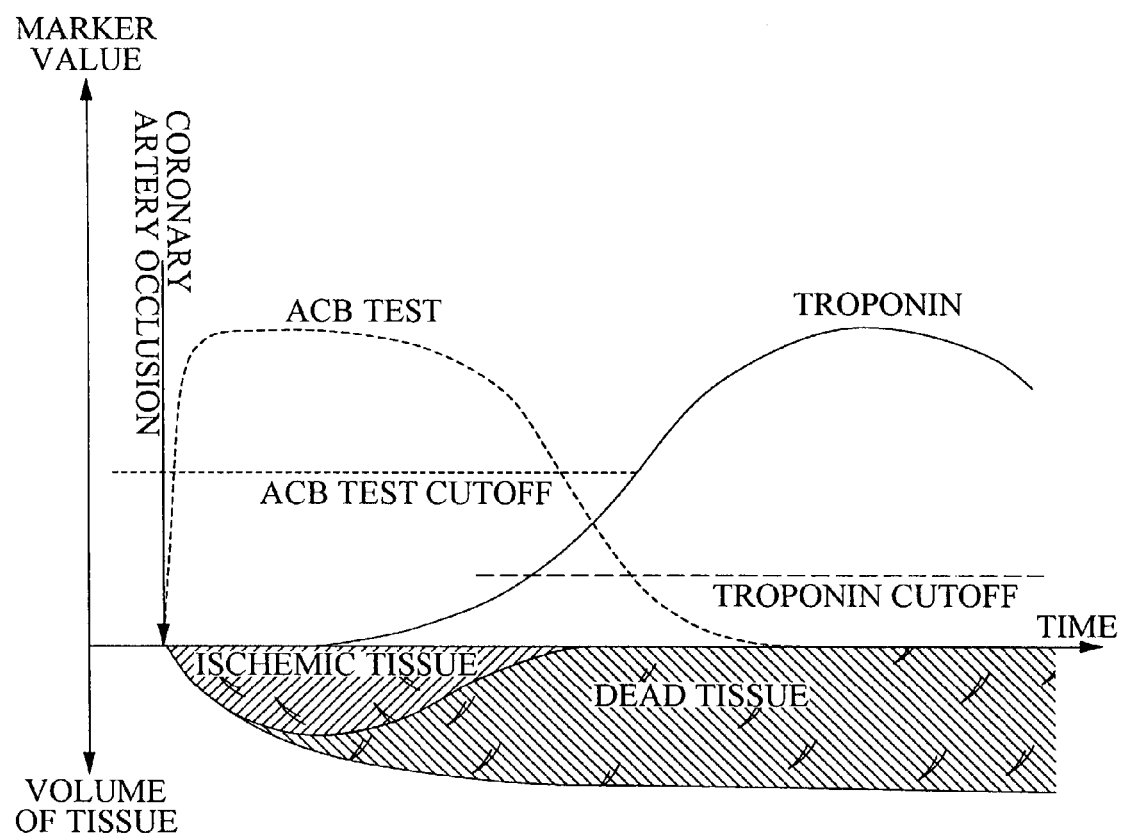
FIG. 4 is a diagrammatic illustration showing the sequence of rise and fall of ischemia modified albumin and troponin after a coronary artery occlusion.

The relationship between IMA and troponin during ACS leading to AMI is illustrated diagrammatically in FIG. 4. The bottom section of the graph represents the volume of tissue which is ischemic or necrosed. The top section of the graph represents the values of the two markers. At the time of a coronary artery occlusion (shown as the vertical arrow at the left of the horizontal time axis), some tissue immediately becomes reversibly ischemic. With the passage of a small amount of time, the tissue which has been reversibly ischemic for the longest time starts to become irreversibly ischemic and will eventually die. As more time passes, more and more of the tissue becomes ischemic, and more of the ischemic tissue becomes necrotic. Eventually, the volume of ischemic tissue starts to decrease, as the ischemic tissue is converted to necrotic tissue. Eventually, all the tissue affected by the coronary artery occlusion is necrotic, and there is a full blown infarct, with no ischemic tissue remaining.

A short time after the coronary artery occlusion, IMA is produced and the ACB Test value rises above the cutoff (i.e.: the upper limit of the normal range), indicating rapidly the presence of ischemic tissue. As time goes on, the ACB Test remains elevated while there is still ischemic tissue, and once all the affected tissue has converted from ischemia to necrosis, the ACB Test starts to fall. As soon as some of the ischemic tissue becomes necrotic, troponin is released and makes its way into the bloodstream. Once there is a sufficient volume of necrotic tissue, and a sufficient time has passed, the serum troponin level rises above the cutoff level.

One of the major limitations of the use of troponin is that because troponin falls slowly after infarct (usually over several days), it is extremely difficult to diagnose re-infarct or subsequent ischemic events. As an example, consider a patient who presents with chest pain, is diagnosed as having an AMI and is treated with reperfusion therapy (e.g., thrombolytics, PTCA, stent or surgery). If this patient presents with another episode of chest pain two or three days after the initial event, with present biochemical markers of necrosis it is extremely difficult to determine if this is another event, because troponin (and possibly CK-MB) will still be elevated due to cardiac damage from the initial AMI. However, since the IMA marker falls so rapidly after an episode, a patient's discharge value of the IMA marker is likely to be within normal range. Thus, if the patient presents with another episode, if the IMA marker is elevated upon presentation the second time, then it is likely to be a second event.

To take advantage of this unique benefit of IMA, a further embodiment of the algorithm includes memory about the patient's previous history. That is, if a patient presents on one date and the diagnosis is STEMI, and then presents a few days later with normal ECG, but elevated troponin, then the addition of IMA can help determine if this presentation is non-ischemic chest pain (i.e.: IMA normal) or another ischemic event (i.e.: IMA elevated).

Since the algorithms described above require evaluation of whether the tests results are above or below a predetermined cutoff, it is not strictly necessary for the test method to produce a quantitative result, although of course a quantitative result gives additional information about timing of the event, particularly if sequential measurements are taken. A quantitative result can also give an indication of the severity of the episode, i.e., the extent of ischemic tissue.

In a further embodiment, serial determinations of an assay for an IMA marker in conjunction with serial testing of ECG and/or serial testing of a marker of necrosis can yield information about the time course of a cardiac ischemic event. Reference to FIG. 4 shows diagramatically the rise and fall of the IMA marker and Troponin for a single event of coronary artery occlusion. Serial determinations of ischemia marker(s) (and optionally other in vitro markers) and serial ECG readings from patient populations presenting with cardiac or suspected cardiac issues, can be combined to create a model or algorithm similar or analogous to that of FIG. 4, which maps the time course of ischemic/necrotic/ECG events for patients undergoing cardiac distress. Physicians may then correlate a particular patient's (serial) readings to the model or algorithm to determine the patient's status or position within the ischemia/necrosis progression and/or determine the time of onset of the acute myocardial infarction, unstable angina, etc.

Although the method has been described in terms of using the ECG in conjunction with biochemical markers which are detected in blood (with serum or plasma), the invention is not restricted to this type of sample. Other substance streams (body fluids or tissue samples) such as urine, saliva, tears, semen, mucus, feces, expired breath and the like could be used. For example, Paz, F. (U.S. Pat. No. 5,515,859 (1996)) disclosed the use of detection of adenosine in an expired breath sample as a possible marker of cardiovascular distress. Adenosine is a potent vasodilator and is produced by tissue in response to stress in an attempt to increase blood flow. Although it is not released from the interior of cells as a result of necrosis, it is released by normal physiological mechanisms by cells. Thus the combination of a measurement of adenosine from expired breath with a measurement of ECG would satisfy one of the objects of the present invention.

In one specific embodiment of the present invention, an electronic module housing is provided which comprises an ECG means and an apparatus for reading or conducting a biochemical test using a test strip. There are many methods of implementing a test strip for an assay as will be known to those familiar with the art. For example, Biosite Inc. (San Diego, Calif.) sells a Triage® Cardiac Reader for quantitative determination of troponin, CK-MB and myoglobin.

Figure 2:
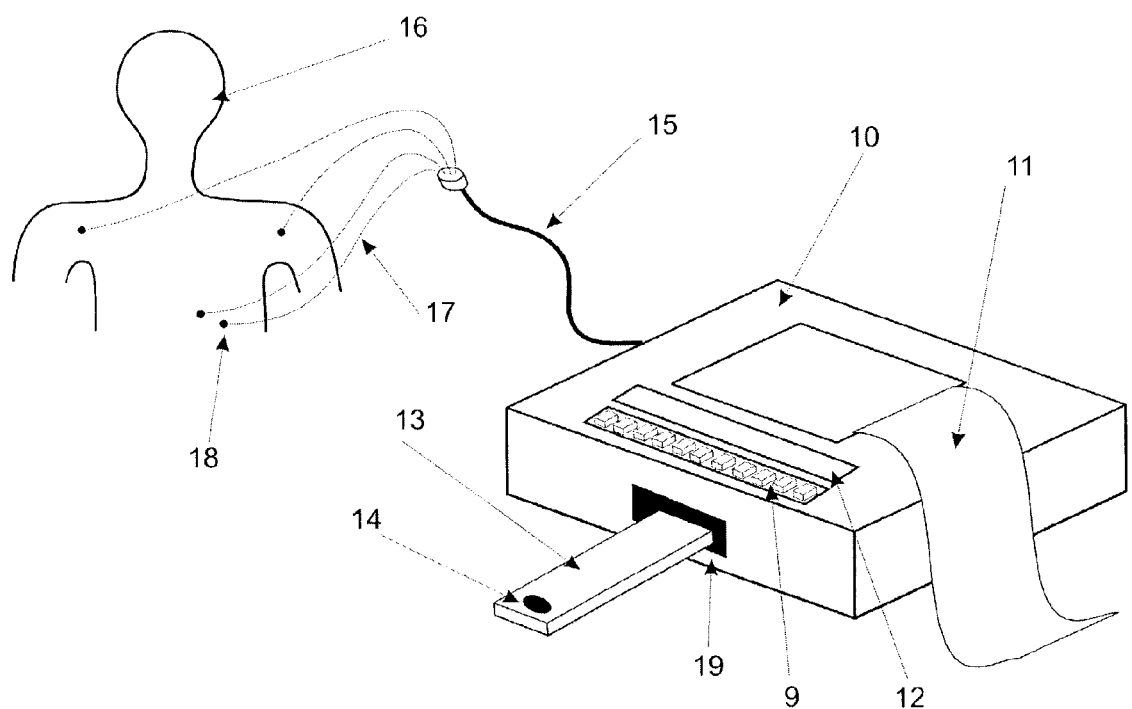
FIG. 2 is a diagrammatic illustration of a device which includes apparatus for ECG analysis in conjunction with apparatus for performing one or more in vitro diagnostic tests.

FIG. 2 is an illustration of such a device. In FIG. 2, the electronic module housing (10) comprises an ECG function means including a means for displaying and/or printing ECG results (11), and a means such as a keyboard by which an operator controls the operation of the machine and enters parameters into the machine (9), and a means by which the operation of the machine is displayed to the operator such as a display panel (12). The machine is connected to the patient (16) via a cable (15). The cable has connected to it a plurality of wires (one is shown as (17)) connected to ECG electrodes (18) placed on the patient's body. The module housing has an aperture or slot into which a test strip is inserted (19), and associated means for reading the results of a test strip for one or more biochemical markers. In the illustration, the reader means is included in the body of the housing module (but it could be separate and connected, for example, via a wire). A test strip (13) has a location (14) such as a well for application of a patient sample. The test strip is inserted into the reader means via an aperture or slot (19).

The term "test strip" refers to assay devices such as those described in U.S. Ser. No. 09/849,956, filed May 4, 2001, which is incorporated herein in its entirety by reference, which typically comprise a carrier media with flow path(s), an application zone for sample deposition, and a test zone for detection and/or measurement of target compounds (ischemic and/or necrotic markers). Although the term "test strip" is used herein, it is intended that configurations other than an elongated assay strip are included within the scope of the subject invention. It is also contemplated that the test strip or like device may be a bar code readable device such as that described in U.S. Ser. No. 09/846,411, filed May 1, 2001, incorporated herein in its entirety by reference. The reader for the test strip will, according to the state of the art, include means for reading the strip's calibration and other parameters, such as a bar code reader.

Figure 3:
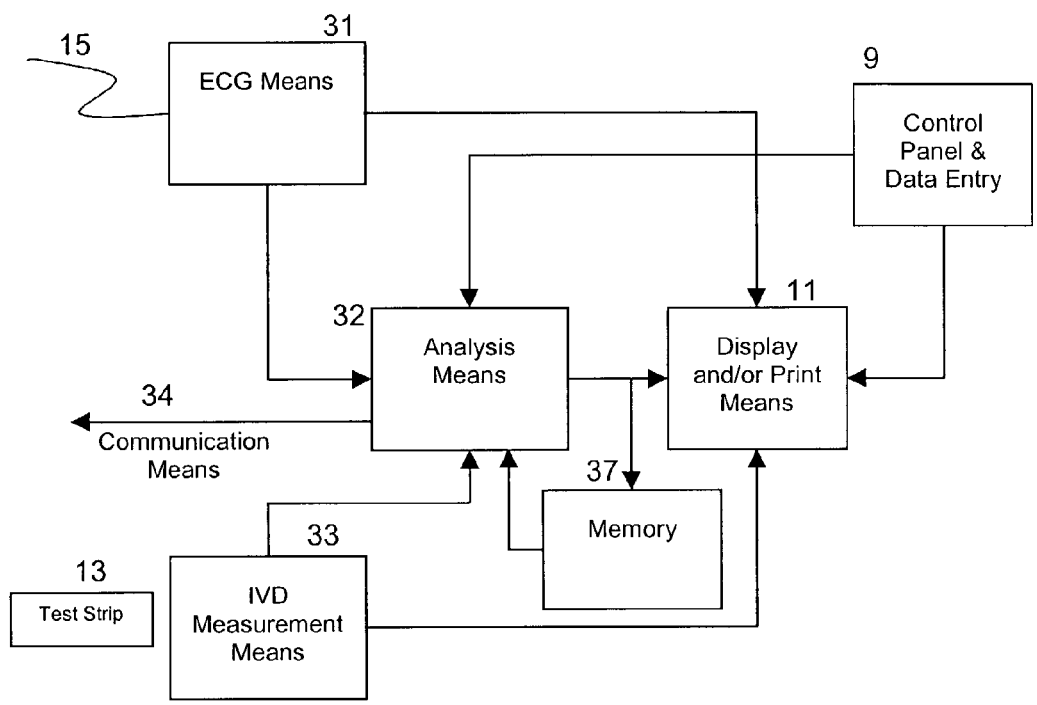
FIG. 3 is a block diagram of the interaction between the ECG machine and the device for performing one or more in vitro diagnostic tests.

FIG. 3 is a block diagram of the interaction between the ECG function of the apparatus and the in vitro diagnostic testing/reading means. A cable (15) connects the patient and the plurality of electrodes to the ECG means (31). The IVD test strip (13) is inserted into the ischemia and/or in vitro diagnostic testing/reader means (33). The ECG means and the testing/reader means include means for analyzing the results, and communicating those results via a signal to an analysis means (32) such as a microprocessor. The analysis means performs the calculations for an algorithm to combine the results of the ECG test and the ischemia and optionally the other in vitro diagnostic tests. The results of the ECG, the ischemia and other measurements, and the analysis of the combined results are displayed and/or printed via a Display and/or print means (11), which is shown as one means for all types of display or print, but could, in fact, be separate means for each type of information to be displayed or printed. A control panel and data entry means (9) is used to control the operation of the machine, and also to enter data (e.g.: patient parameters such as nature of chest pain) which may be used as part of the algorithm in the analysis means.

The clinical performance of any set of diagnostic tools depends on the statistical power of the clinical studies which were employed to determine the statistics of the tool. Such clinical studies are performed on a population with limited numbers, and often of very precise composition. Each clinical setting in which the tools are to be used is likely to have a different patient population with variations in variables such as age, gender, ethnicity, diet, and average body weight. All of these factors may contribute to a modification of the assessment of the risk that a patient presenting with chest pain has ACS.

In a further embodiment of the present invention, the apparatus includes a memory means (item (37) in FIG. 3) used for storing information. As a patient's data is analyzed by the apparatus, the input and output parameters are stored in the memory means. At some later time, the operator can enter via the control panel (9) the clinical outcome of the patient (or the outcome can be made available automatically, e.g.: via a communication means (34) connected with the hospital's internal information system). In this way, the data in the memory is updated and compared with the clinical outcome, and the algorithm embodied in the analysis means (32) can be modified appropriately in response to the new comparisons from this and other patients to provide improved performance on next use.

There are many methods well known in the art for implementing such a heuristic process, including a neural network. The heuristic algorithm can be implemented entirely in the apparatus itself, or could reside on a central computer system with which the combined ECG machine and test strip apparatus communicates via a communication means (34), which can be a physical connection or a virtual one, such as via the internet. In this latter example, the algorithm of each machine so connected to the central computer system can be updated and improved every time additional comparison information is available from any machine connected to the network.

EXAMPLES

Example 1

The ACB Test Used for Diagnosis of Acute Coronary Syndromes

A study was performed to investigate the performance of IMA for early risk stratification of patients presenting with chest pain (or equivalent) of suspected cardiac origin. The performance of IMA was compared with troponin T and the presentation 12 lead ECG. The end point was discharge diagnosis of ACS (STEMI, NSTEMI or UA) or Non Ischemic Chest Pain (NICP), as a measure of short term risk at presentation.

Patients who arrived at the Emergency Department (ED) with clinical signs and symptoms of possible ACS within 3 hours from symptom onset were enrolled. All patients had a 12 lead ECG and a blood sample collected within 1–2 hours of arrival to the ED. IMA and cTnT (Roche Diagnostics) testing was performed on each presentation sample.

Data Analysis

ECGs with no ST segment shift or T wave changes (apart from lead III or V1) were considered "negative". "Positive" ECGs were those with ST segment depression or elevation ≧1 mV, or T wave inversion ≧2 mV (in ≧2 consecutive leads). Equivocal or uninterpretable ECGs (e.g.: left bundle branch block, paced rhythm, extensive pathological Q waves, and/or persistent ST-segment elevation following previous AMI) were considered to be "negative" in this study.

ACB Test results >85 U/mL were considered positive based on a previously performed Normal Range Study.

Cardiac troponin T was measured by electrochemiluminescence assay with an Elecsys 2010 analyzer (Roche Diagnostics). cTnT concentrations >0.05 ng/mL were considered positive.

Institutional discharge diagnosis of ST-elevation AMI (STEMI), non ST-elevation AMI (NSTEMI), unstable angina (UA), and non-ischemic chest pain (NICP) were determined according to institutional guidelines based upon the ESC/ACC criteria for diagnosis of AMI and the ACC/AHA guidelines for diagnosis of unstable angina. STEMI, NSTEMI, and UA were considered diagnoses of high risk. A diagnosis of NICP was considered low risk.

Diagnosis of acute myocardial infarction (AMI) was confirmed if ESC/ACC criteria were fulfilled, using a cTnT cutoff of 0.05 ng/mL. AMI was labeled as ST elevation myocardial infarction (STEMI) or non-ST segment elevation myocardial infarction (NSTEMI) based on ECG and biochemical criteria, i.e., cTnT>0.05 ng/ml.

Unstable angina (UA) was diagnosed when there was acute chest pain without myocardial necrosis (i.e.: no elevation of cTnT), but with clinical evidence of reduced myocardial perfusion, positive ECG/echocardiographic stress testing or significant lesions on coronary angiography.

Discharge diagnosis of ACS includes AMI and UA.

Patients with documented non-cardiac causes of chest pain and/or normal coronary angiography were classified as non-ischemic chest pain (NICP).

Results

The total study population included 140 men and 68 women. Mean age was 61.3 years (range 21–85); 49 (23.5%) were smokers; 31 (15%) were diabetic; 93 (44%) were hypertensive; 65 (31%) had family history of coronary artery disease; and 73 (35%) were treated for hypercholesterolemia.

The data were analyzed for seven cases:
1. IMA alone
2. Troponin T alone
3. ECG alone
4. Combination of troponin T and IMA (denoted as TnT & IMA in the following tables)
5. Combination of ECG and IMA (denoted as ECG & IMA in the following tables)
6. Combination of ECG and troponin T (denoted as ECG & TnT in the following tables)
7. Combination of ECG and troponin T and IMA (denoted as ECG & TnT & IMA in the following tables)

Results of IMA, ECG, and cTnT were analyzed for clinical sensitivity, specificity, positive predictive value (PPV), and negative predictive value (NPV), alone and in combination. The 2 and 3 test combinations of IMA, ECG, and cTnT were considered positive if any one of the tests was positive, and negative if all were negative. Performance estimates were compared using McNemar's test for correlated proportions and confidence intervals were calculated using the exact binomial method. A two tailed p-value of <0.05 was considered significant. The data are presented below in contingency tables.

Sensitivity of each diagnostic test is shown for the total population of 131 acute coronary syndrome (ACS) patients and also for the 20 ST elevation MI (STEMI) patients, the 26 non-ST Elevation MI (NSTEMI) patients, and the 85 unstable angina patients. Specificity estimates are based upon 77 patients diagnosed with non-ischemic chest pain (NICP). In the tables below "+ve" is an abbreviation for "positive" and "−ve" is an abbreviation for "negative".

IMA Alone

|  | STEMI | NSTEMI | UA | Total +ve ACS | Total −ve ACS | Grand Totals | % 95% CI |
|---|---|---|---|---|---|---|---|
| IMA +ve | 12 | 18 | 77 | 107 | 42 | 149 | PPV 71.8% 63.9–78.9 |
| IMA −ve | 8 | 8 | 8 | 24 | 35 | 59 | NPV 59.3% 45.7–71.9 |
| Total | 20 | 26 | 85 | 131 | 77 | 208 | |
| 95% CI | Sensitivity 60.0% 36.1–80.9 | Sensitivity 69.2% 48.2–85.7 | Sensitivity 90.6% 82.3–95.8 | Sensitivity 81.7% 74.0–87.9 | Specificity 45.5% 34.1–57.2 | | |

ECG Alone

|  | STEMI | NSTEMI | UA | Total +ve ACS | Total −ve ACS | Grand Totals | % 95% CI |
|---|---|---|---|---|---|---|---|
| ECG +ve | 19 | 13 | 27 | 59 | 7 | 66 | PPV 89.4% 79.4–95.6 |
| ECG −ve | 1 | 13 | 58 | 72 | 70 | 142 | NPV 49.3% 40.8–57.8 |
| Total | 20 | 26 | 85 | 131 | 77 | 208 | |
| 95% CI | Sensitivity 95.0% 75.1–99.9 | Sensitivity 50.0% 29.9–70.1 | Sensitivity 31.8% 22.1–42.8 | Sensitivity 45.0% 36.3–54.0 | Specificity 90.0% 82.2–96.3 | | |

TnT Alone

|  | STEMI | NSTEMI | UA | Total +ve ACS | Total −ve ACS | Grand Totals | % 95% CI |
|---|---|---|---|---|---|---|---|
| TnT +ve | 6 | 17 | 3 | 26 | 1 | 27 | PPV 96.3% 81.0–99.9 |
| TnT −ve | 14 | 9 | 82 | 105 | 76 | 181 | NPV 42.0% 34.7–49.5 |
| Total | 20 | 26 | 85 | 131 | 77 | 208 | |
| 95% CI | Sensitivity 30.0% 11.9–54.3 | Sensitivity 65.4% 44.3–82.8 | Sensitivity 3.5% 0.7–10.0 | Sensitivity 19.8% 13.4–27.7 | Specificity 98.7% 93.0–100.0 | | |

TnT and IMA in Combination (either positive is +ve, both negative is −ve)

|  | STEMI | NSTEMI | UA | Total +ve ACS | Total −ve ACS | Grand Totals | % 95% CI |
|---|---|---|---|---|---|---|---|
| Either +ve | 15 | 25 | 78 | 118 | 43 | 161 | PPV 73.3% 65.8–79.9 |
| Both −ve | 5 | 1 | 7 | 13 | 34 | 47 | NPV 72.3% 57.4–84.4 |
| Total | 20 | 26 | 85 | 131 | 77 | 208 | |
| 95% CI | Sensitivity 75.0% 50.9–91.3 | Sensitivity 96.2% 80.4–99.9 | Sensitivity 91.8% 83.8–96.6 | Sensitivity 90.1% 83.6–94.6 | Specificity 44.2% 32.8–55.9 | | |

| | ECG and IMA in Combination (either positive is +ve, both negative is −ve) | | | | | | |
|---|---|---|---|---|---|---|---|
| | STEMI | NSTEMI | UA | Total +ve ACS | Total −ve ACS | Grand Totals | % 95% Cl |
| Either +ve | 20 | 21 | 80 | 121 | 44 | 165 | PPV 73.3% 65.9–79.9 |
| Both −ve | 0 | 5 | 5 | 10 | 33 | 43 | NPV 76.7% 61.4–88.2 |
| Total | 20 | 26 | 85 | 131 | 77 | 208 | |
| 95% Cl | Sensitivity 100% 83.2–100.0 | Sensitivity 80.8% 60.6–93.4 | Sensitivity 94.1% 86.8–98.1 | Sensitivity 92.4% 86.4–96.3 | Specificity 42.9% 31.6–54.6 | | |

| | ECG and TnT in Combination (either positive is +ve, both negative is −ve) | | | | | | |
|---|---|---|---|---|---|---|---|
| | STEMI | NSTEMI | UA | Total +ve ACS | Total −ve ACS | Grand Totals | % 95% Cl |
| Either +ve | 19 | 21 | 29 | 69 | 8 | 77 | PPV 89.6% 80.6–95.4 |
| Both −ve | 1 | 5 | 56 | 62 | 69 | 131 | NPV 52.7% 43.8–61.5 |
| Total | 20 | 26 | 85 | 131 | 77 | 208 | |
| 95% Cl | Sensitivity 95.0% 75.1–99.9 | Sensitivity 80.8% 60.6–93.4 | Sensitivity 34.1% 24.2–45.2 | Sensitivity 52.7% 43.8–61.5 | Specificity 89.6% 80.6–95.4 | | |

| | ECG and TnT and IMA in Combination (any positive is +ve, all negative is −ve) | | | | | | |
|---|---|---|---|---|---|---|---|
| | STEMI | NSTEMI | UA | Total +ve ACS | Total −ve ACS | Grand Totals | % 95% Cl |
| Any +ve | 20 | 25 | 80 | 125 | 45 | 170 | PPV 73.5% 66.2–80.0 |
| All −ve | 0 | 1 | 5 | 6 | 32 | 38 | NPV 84.2% 68.7–94.0 |
| Total | 20 | 26 | 85 | 131 | 77 | 208 | |
| 95% Cl | Sensitivity 100% 83.2–100.0 | Sensitivity 96.2% 80.4–99.9 | Sensitivity 94.1% 86.8–98.1 | Sensitivity 95.4% 90.3–98.3 | Specificity 41.6% 30.4–53.4 | | |

Figure 5:
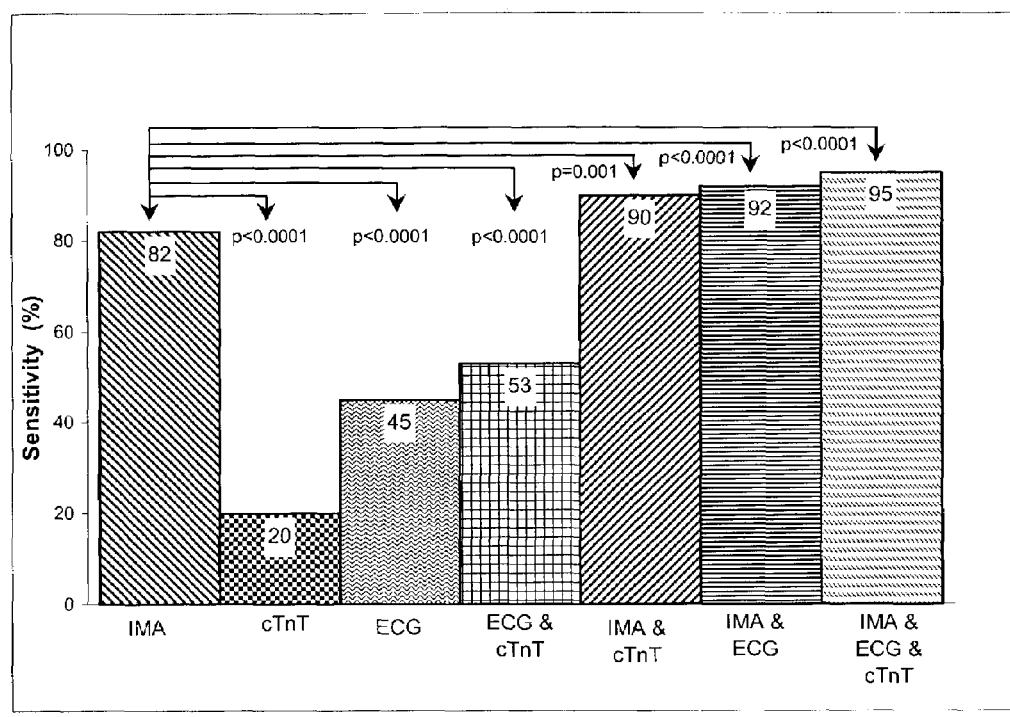
FIG. 5 is a graph of sensitivity for detection of ACS for ECG, cardiac troponin T, and IMA.

The sensitivities of presentation IMA, cTnT, ECG and combinations of these tests were compared for statistically significant differences. FIG. 5 illustrates the sensitivity of IMA alone and in conjunction with ECG and cTnT. IMA at presentation identified 107 of 131 ACS patients (82%, 95% Confidence Interval (CI) 74–88, compared to 59 of 131 (45%, CI 36–54) by admission ECG and 26 of 131 (20%, CI 13–28) by admission cTnT. When IMA was used with ECG, the sensitivity increased to 92% (CI 86–96) and this was similar to that of IMA used with cTnT, 90% (CI 84–95). Sensitivity of the three tests combined was 95% (CI 90–98), which was significantly greater than that of IMA and cTnT combined (p=0.02) and statistically equivalent to the sensitivity of IMA and ECG combined (p=0.13). When ECG and cTnT were used, as per standard practice, 53% (CI 44%–62%) of patients with chest pain of ischemic origin were identified.

Logistic regression was used to construct predictive models for final diagnosis. IMA and cTnT were treated as quantitative and ECG as qualitative. The area under the Receiver Operator Characteristic (ROC) curve was evaluated for each model's ability to discriminate ACS from NICP. A p value <0.05 was considered significant. The ROC curve for IMA alone is shown in FIG. 6, and the area under the curve is 0.68 (95% CI 0.61–0.76). The results of this analysis are shown in Table 2. In this table, it can be seen that the addition of IMA to ECG provides more diagnostic power than either parameter alone, and the combination of IMA, ECG, and troponin T provides more diagnostic power in combination than any single alone, or any pair together.

TABLE 2

| Logistic regression model | Chi Square for model | p value for model | Significant variables | Area under ROC curve (95% CI) |
|---|---|---|---|---|
| IMA alone | 23.13 | <0.0001 | IMA | 0.68 (0.61–0.76) |
| ECG alone | 32.70 | <0.0001 | ECG | 0.68 (0.61–0.75) |
| cTnT alone | 20.73 | <0.0001 | cTnT | 0.64 (0.56–0.72) |
| ECG + cTnT | 47.30 | <0.0001 | ECG | 0.74 (0.68–0.81) |
| IMA + ECG | 55.38 | <0.0001 | IMA and ECG | 0.80 (0.74–0.86) |
| IMA + cTnT | 49.15 | <0.0001 | IMA and cTnT | 0.77 (0.70–0.83) |
| IMA + ECG + cTnT | 74.10 | <0.0001 | IMA and ECG | 0.83 (0.78–0.89) |

The parameters from the logistic regression analysis were used to construct curves of the probability of ACS, p[ACS], vs IMA value, cTnT value, and the two combined.

Figure 7:
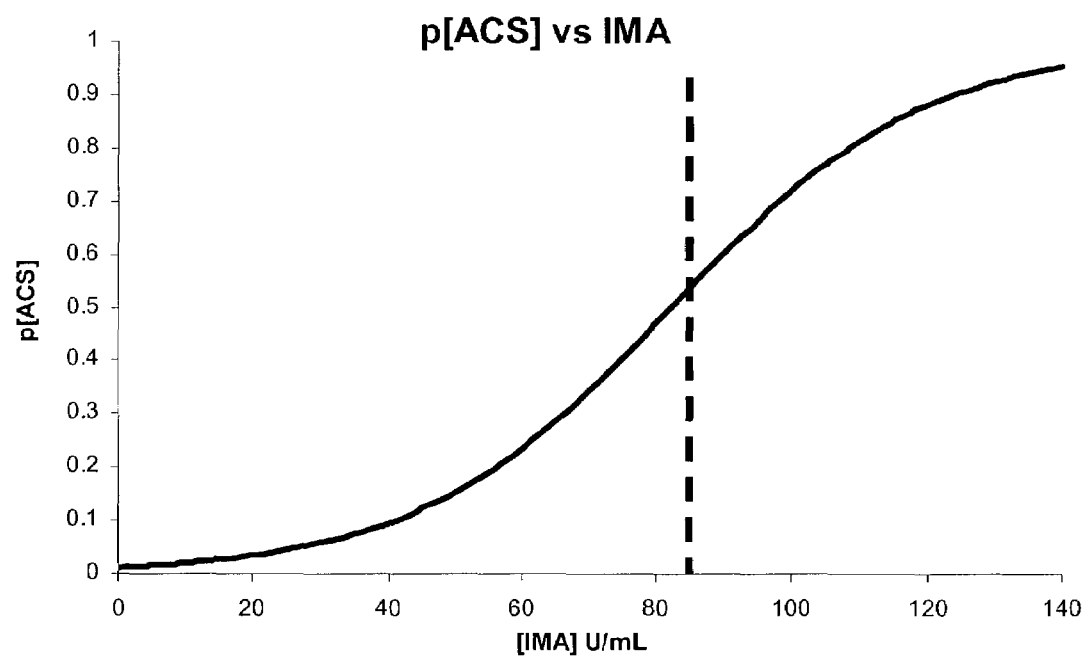
FIG. 7 is a graph of the probability of ACS vs value of IMA alone.

FIG. 7 shows p[ACS] vs IMA, with the 95th percentile upper limit of normal cutoff shown as a vertical line. This indicates that IMA values higher than 100 are strongly suggestive of ACS (for example, p[ACS]>80% for [IMA] >110 U/mL), and IMA values less than 70 are strongly suggestive of no ACS (e.g.: p[ACS]<35% for [IMA]<70 U/mL).

Figure 8:
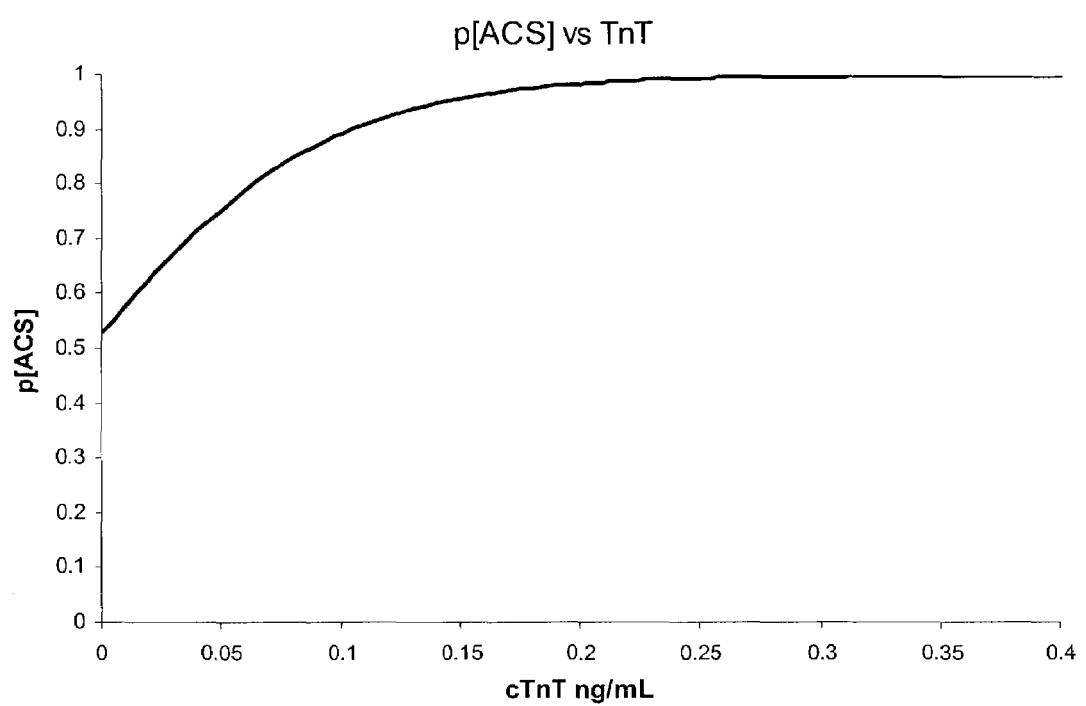
FIG. 8 is a graph of the probability of ACS vs value of troponin T alone.

FIG. 8 shows the probability of ACS with different values of cTnT. This demonstrates that any elevation of cTnT above the cutoff of 0.05 ng/mL is highly significant for ACS (e.g.: p[ACS]>86% for [cTnT]>0.1 ng/mL). However, consistent with the published literature, the data also show that a negative cTnT has no value for rule out, since the p[ACS] is still >0.5 for [cTnT]=0.

Figure 9:
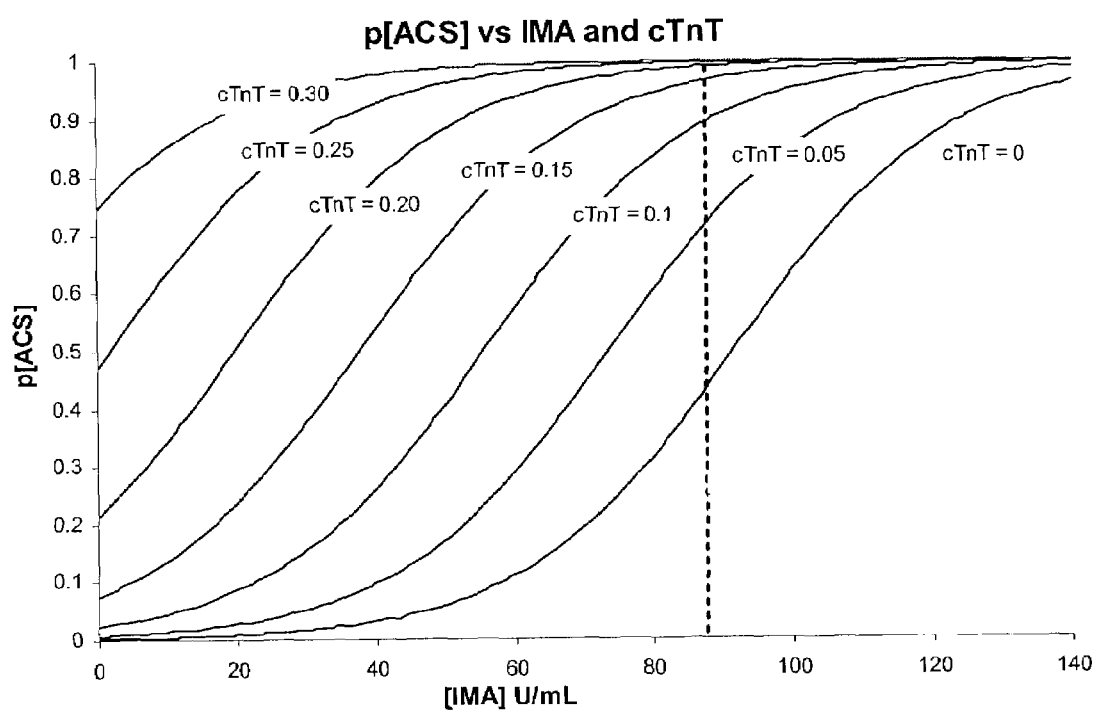
FIG. 9 is a graph of the probability of ACS using troponin and IMA combined.

FIG. 9 shows a family of curves of p[ACS] vs [IMA] for different values of [cTnT], with a vertical line at the ACB Test value of 85—the 95th percentile of the upper limit of normal. These curves demonstrate that the major clinical value of IMA is in patients where c[TnT] is zero—which, of course, is the majority of patients at presentation. However, IMA may be helpful in resolving cases with low values of [cTnT] near the cutoff of 0.05 ng/mL. For example, if [cTnT]=0.5 ng/mL, and [IMA]>100, then p[ACS]>90%. On the other hand, if [cTnT]=0.05 ng/mL, and [IMA]<60 U/mL, then p[ACS]<25%.

Example 2

IMA for Risk Stratification of Chest Pain Patients

This study was designed to investigate the performance of IMA, ECG, and troponin T at acute presentation for early risk stratification of patients with chest pain suggestive of cardiac origin. The study was performed in a low to medium risk patient population referred for rest myocardial perfusion imaging (MPI) on presentation.

The institutional discharge diagnosis of ACS (i.e.: a measure of short term risk) was used for data analysis presented in this section. Serum specimens were drawn prospectively and assayed at one of two core laboratories with the ACB Test and cardiac troponin T assays.

One blood specimen was drawn prior to injection of the perfusion agent (the presentation draw or an additional baseline draw was taken if the MPI study was scheduled >1 hr from presentation). Another blood draw was taken one hour post injection of the myocardial perfusion agent. All of these blood draws were consistent with the timing of blood taken in Study #1 which was while the patient was still in pain or within 3 hours of feeling pain. IMA was measured by the Albumin Cobalt Binding Test (ACB® Test) on the Roche Cobas MIRA® PLUS.

Data Analysis

ECGs with no ST segment shift or T wave changes (apart from lead III or V1) were considered "negative". "Positive" ECGs were those with ST segment depression or elevation ≧1 mV, or T wave inversion ≧2 mV (in ≧2 consecutive leads). Equivocal or uninterpretable ECGs (i.e. left bundle branch block, paced rhythm, extensive pathological Q waves, and/or persistent ST-segment elevation following previous AMI) were considered to be "negative" in this study. Institutional discharge diagnosis of ST-elevation AMI (STEMI), non ST-elevation AMI (NSTEMI), unstable angina (UA), and non-ischemic chest pain (NICP) were determined according to institutional guidelines based upon the ESC/ACC criteria for diagnosis of AMI and the ACC/AHA guidelines for diagnosis of unstable angina. STEMI, NSTEMI, and UA were considered diagnoses of high risk. A diagnosis of NICP was considered low risk.

Diagnosis of acute myocardial infarction (AMI) was confirmed if ESC/ACC criteria were fulfilled, using a cTnT cutoff of 0.05 ng/mL. AMI was labeled as ST elevation myocardial infarction (STEMI) or non-ST segment elevation myocardial infarction (NSTEMI) based on ECG and biochemical criteria i.e. cTnT>0.05 ng/ml.

Unstable angina (UA) was diagnosed when there was acute chest pain without myocardial necrosis (i.e.: no elevation of cTnT), but with clinical evidence of reduced myocardial perfusion, positive ECG/echocardiographic stress testing or significant lesions on coronary angiography.

Discharge diagnosis of ACS includes AMI and UA.

Patients with documented non-cardiac causes of chest pain and/or normal coronary angiography were classified as non-ischemic chest pain (NICP).

ACB Test values >85 U/mL were considered positive based on a previously performed Normal Range Study. An ACB Test result >85 U/mL in any blood draw taken within 3 hours of presentation was taken as a positive ACB Test.

Cardiac troponin T concentrations were measured according to the package insert by electrochemiluminescence assay with an Elecsys 2010 analyzer (Roche Diagnostics). cTnT concentrations >0.05 ng/mL were considered positive. A troponin >0.05 ng/mL in any blood draw taken within 3 hours of presentation was taken as a positive troponin for the data analysis.

Results

Data were analyzed from patients recruited at 8 clinical trial sites. Samples were analyzed at one of two core laboratories. Clinical data and assay results were analyzed for a total of 199 patients. Results of IMA, ECG, and cTnT were analyzed for clinical sensitivity, specificity, positive predictive value (PPV), and negative predictive value (NPV), alone and in combination. The 2 and 3 test combinations of IMA, ECG, and cTnT were considered positive if any one of the tests was positive, and negative if all were negative.

The "gold standard" was the discharge diagnosis of ACS.

The data were analyzed (in the same manner as in Study #1 described above for seven cases as listed below and illustrated in the tables on the following pages:

1. IMA alone
2. Troponin T alone
3. ECG alone
4. Combination of troponin T and IMA (denoted as TnT & IMA in the following tables)
5. Combination of ECG and IMA (denoted as ECG & IMA in the following tables)
6. Combination of ECG and troponin T (denoted as ECG & TnT in the following tables)
7. Combination of ECG and troponin T and IMA (denoted as ECG & TnT & IMA in the following tables)

| | | | | IMA Alone | | | |
|---|---|---|---|---|---|---|---|
| | STEMI | NSTEMI | UA | Total +ve ACS | Total −ve ACS | Grand Totals | % 95% Cl |
| IMA +ve | 0 | 4 | 8 | 12 | 119 | 131 | PPV 9.2% 4.8–15.5 |
| IMA −ve | 1 | 1 | 0 | 2 | 66 | 68 | NPV 97.1% 89.8–99.6 |
| Total | 0 | 5 | 8 | 14 | 185 | 199 | |
| 95% Cl | Sensitivity 0.0% 0.0–97.5 | Sensitivity 80.0% 28.4–99.5 | Sensitivity 100.0% 63.1–100.0 | Sensitivity 85.7% 57.2–98.2 | Specificity 35.7% 28.8–43.0 | | |

| | | | | ECG Alone | | | |
|---|---|---|---|---|---|---|---|
| | STEMI | NSTEMI | UA | Total +ve ACS | Total −ve ACS | Grand Totals | % 95% Cl |
| ECG +ve | 1 | 2 | 0 | 3 | 13 | 16 | PPV 18.8% 4.0–45.6 |
| ECG −ve | 0 | 3 | 8 | 11 | 172 | 183 | NPV 94.0% 89.5–97.0 |
| Total | 1 | 5 | 8 | 14 | 185 | 199 | |
| 95% Cl | Sensitivity 100.0% 2.5–100.0 | Sensitivity 40.0% 5.3–85.3 | Sensitivity 0.0% 0.0–36.9 | Sensitivity 21.4% 4.7–50.8 | Specificity 93.0% 88.3–96.2 | | |

| | | | | TnT Alone | | | |
|---|---|---|---|---|---|---|---|
| | STEMI | NSTEMI | UA | Total +ve ACS | Total −ve ACS | Grand Totals | % 95% Cl |
| TnT +ve | 1 | 5 | 1 | 7 | 2 | 9 | PPV 77.8% 40.0–97.2 |

-continued

TnT Alone

| | STEMI | NSTEMI | UA | Total +ve ACS | Total −ve ACS | Grand Totals | % 95% Cl |
|---|---|---|---|---|---|---|---|
| TnT −ve | 0 | 0 | 7 | 7 | 183 | 190 | NPV 96.3% 92.6–98.5 |
| Total 95% Cl | 1 Sensitivity 100.0% 2.5–100.0 | 5 Sensitivity 100.0% 47.8–100 | 8 Sensitivity 12.5% 0.3–52.7 | 14 Sensitivity 50.0% 23.0–77.0 | 185 Specificity 98.9% 96.1–99.9 | 199 | |

TnT and IMA in Combination (either positive is +ve, both negative is −ve)

| | STEMI | NSTEMI | UA | Total +ve ACS | Total −ve ACS | Grand Totals | % 95% Cl |
|---|---|---|---|---|---|---|---|
| Either +ve | 1 | 5 | 8 | 14 | 121 | 135 | PPV 10.4% 5.8–16.8 |
| Both −ve | 0 | 0 | 0 | 0 | 64 | 64 | NPV 100.0% 94.4–100.0 |
| Total 95% Cl | 1 Sensitivity 100.0% 2.5–100.0 | 5 Sensitivity 100.0% 47.8–100.0 | 8 Sensitivity 100.0% 63.1–100.0 | 14 Sensitivity 100.0% 76.8–100.0 | 185 Specificity 34.6% 27.8–41.9 | 199 | |

ECG and IMA in Combination (either positive is +ve, both negative is −ve)

| | STEMI | NSTEMI | UA | Total +ve ACS | Total −ve ACS | Grand Totals | % 95% Cl |
|---|---|---|---|---|---|---|---|
| Either +ve | 1 | 5 | 8 | 14 | 122 | 136 | PPV 10.3% 5.7–16.7 |
| Both −ve | 0 | 0 | 0 | 0 | 63 | 63 | NPV 100% 94.3–100.0 |
| Total 95% Cl | 1 Sensitivity 100% 2.5–100 | 5 Sensitivity 100.0% 28.4–99.5 | 8 Sensitivity 100.0% 63.1–100 | 14 Sensitivity 100.0% 76.8–100.0 | 185 Specificity 34.1% 27.3–41.4 | 199 | |

ECG and TnT in Combination (either positive is +ve, both negative is −ve)

| | STEMI | NSTEMI | UA | Total +ve ACS | Total −ve ACS | Grand Totals | % 95% Cl |
|---|---|---|---|---|---|---|---|
| Either +ve | 1 | 5 | 1 | 7 | 15 | 22 | PPV 31.8% 13.9–54.9 |
| Both −ve | 0 | 0 | 7 | 7 | 170 | 177 | NPV 96.0% 92.0–98.4 |
| Total 95% Cl | 1 Sensitivity 100.0% 2.5–100 | 5 Sensitivity 100.0% 47.8–100.0 | 8 Sensitivity 12.5% 0.3–52.7 | 14 Sensitivity 50.0% 23.0–77.0 | 185 Specificity 91.9% 87.0–95.4 | 199 | |

ECG and TnT and IMA in Combination (any positive is +ve, all negative is -ve)

| | STEMI | NSTEMI | UA | Total +ve ACS | Total -ve ACS | Grand Totals | % 95% CI |
|---|---|---|---|---|---|---|---|
| Any +ve | 1 | 5 | 8 | 14 | 124 | 138 | PPV 10.1% 5.7–16.4 |
| All -ve | 0 | 0 | 0 | 0 | 61 | 61 | NPV 100.0% 94.1–100.0 |
| Total 95% CI | 1 Sensitivity 100% 2.5–100.0 | 5 Sensitivity 100.0% 47.8–100.0 | 8 Sensitivity 100.0% 63.1–100.0 | 14 Sensitivity 100.0% 76.8–100.0 | 185 Specificity 33.0% 26.3–40.3 | 199 | |

Figure 10:
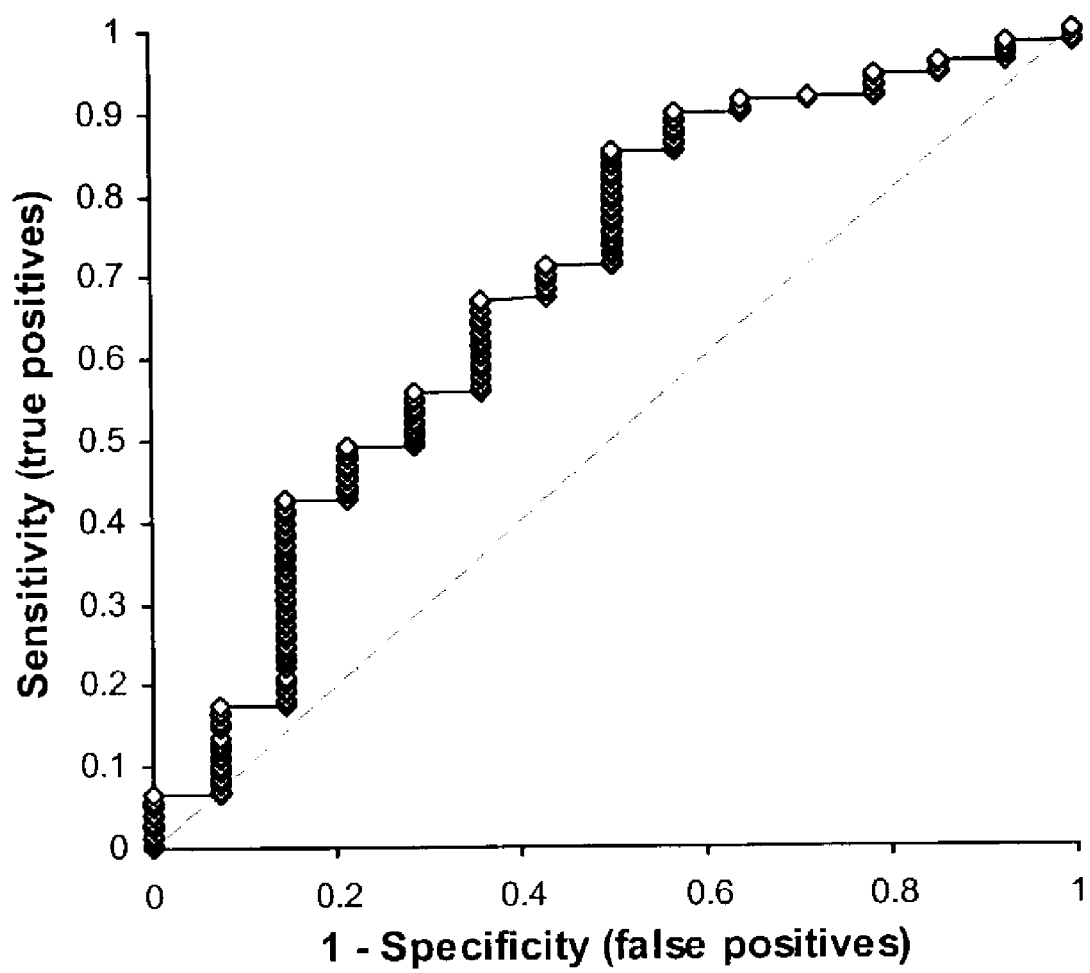
FIG. 10 is a graph of the ROC curve for IMA for detection of ACS from Study 2.

Logistic regression was used to construct a predictive model for final diagnosis using IMA as a quantitative variable. The ROC curve is shown in FIG. 10, and the area under the ROC curve is 0.68 (95% CI 0.53–0.84), which is equivalent to that found in the previous study, above.

This study showed that in a population of patients with chest pain suggestive of cardiac origin with low prevalence of ACS, IMA showed equivalent sensitivity, and specificity, but higher negative predictive value, to that shown in the previous study.

The sensitivity of presentation IMA for ACS (85.7%) is much greater than that of TnT (50%). The combination of IMA and TnT results in no false negatives and 100% negative predictive value.

The use of IMA and cTnT in combination shows 100% sensitivity and identifies more patients with ACS, which will drive earlier therapy.

Based on the examples described above, it is clear that the combination of ECG with a marker of ischemia such as IMA, and optionally another in vitro diagnostic test such as a marker of cell death such as troponin, can be used to give higher confidence in a diagnosis or risk stratification for a patient presenting to a hospital emergency room with chest pain suggestive of cardiac origin, or can be used in an algorithm to determine a probability of ACS.

It should be understood that the examples and embodiments described herein are for illustrative purposes only and that various modifications or changes in light thereof will be suggested to persons skilled in the art and are to be included within the spirit and purview of this application and the scope of the appended claims.

What we claim is:

1. A method for diagnosis of a clinical condition in a patient, said clinical condition selected from the group consisting of acute cardiac ischemia (ACI), acute coronary syndrome (ACS) or unstable angina (UA), or for risk stratification of a patient possibly with the condition, comprising the steps of:
   a) obtaining from the patient at least one sample of a substance stream which has been in contact with a tissue suspected of undergoing the clinical condition;
   b) conducting at least a first in vitro diagnostic assay on the sample for albumin that has been modified by exposure to ischemic tissue and optionally additional in vitro diagnostic assays;
   c) measuring and analyzing the patient's electrocardiogram (ECG); and
   d) applying an algorithm to combine the results of the assay(s) of step (b) and the electrocardiogram in step
   (c) using an algorithm to provide a positive or negative diagnosis or risk stratification of the clinical condition.

2. The method of claim 1 where the substance stream is selected from the group consisting of whole blood, serum, plasma, saliva, urine, feces, semen, mucus, tears, breath, or sweat.

3. The method of claim 2, wherein the marker for ischemia is ischemia modified albumin.

4. The method of claim 1 further comprising, the steps of:
   e) storing the results of the assay(s) from the stream sample and ECG results for the patient in a memory means;
   f) storing a clinical outcome of the patient into the memory means;
   g) comparing assay and ECG results in the memory with the clinical outcome;
   h) modifying the algorithm in response to the comparison to provide improved diagnosis or risk stratification; and
   i) repeating steps (a)–(h) with a plurality of patients whereby an improved algorithm is provided.

5. The method of claim 1, wherein the clinical event is an acute myocardial infarction.

6. The method of claim 1 wherein the clinical event is stable angina.

7. The method of claim 1 wherein the clinical event is unstable angina.

8. The method of claim 1 wherein the clinical event is acute coronary syndrome.

9. The method of claim 1, wherein the additional in vitro diagnostic assay is an assay for a necrosis marker selected from the group consisting of troponin, CK-MB and myoglobin.

10. The method of claim 9, wherein the algorithm provides for a positive diagnosis or indication of higher risk of ACS, ACI or UA if the ECG is non-diagnostic or normal, the additional in vitro assay for the marker of necrosis is negative and the in vitro assay for modified albumin is positive.

11. The method of claim 1, wherein the additional in vitro diagnostic assay is an assay for B-type natriuretic peptide (BNP) or associated molecules.

12. The method of claim 1, wherein the additional in vitro diagnostic assay is an assay for C Reactive Protein (CRP).

13. The method of claim 1, wherein the additional in vitro diagnostic assay is an assay for adenosine in expired breath.

14. The method of claim 1, wherein the modified albumin assay is selected from the group consisting of an albumin cobalt binding (ACB®) test, an electrochemical test for ischemia modified albumin, an optical test for ischemia modified albumin, an immunoassay for ischemia modified albumin, and a metal affinity assay for ischemia modified albumin.

15. The method of claim 1, wherein the algorithm provides a negative diagnosis or indication of lower risk of ACS, ACI or UA if the ECG is either non-diagnostic or normal, and the modified albumin assay result is negative.

16. The method of claim 1, wherein the algorithm provides a negative diagnosis or indication of lower risk of ACS, ACI or UA if the ECG is either non-diagnostic or normal, and a majority of the modified albumin and additional in vitro assay results are negative.

17. The method of claim 1, wherein the algorithm provides a positive diagnosis or elevated risk stratification of ACS, ACI or UA if the ECG is normal or non-diagnostic and at least one of the modified albumin and additional in vitro diagnostic assays is positive.

18. The method of claim 1, wherein the algorithm provides a positive diagnosis or indication of higher risk of ACS, ACI or UA if the ECG is positive and at least one of the modified albumin or additional in vitro diagnostic assays is positive.

19. The method of claim 1, further comprising repetition of steps (a) and (b) and/or repetition of step (c), followed by repetition of step (d), whereby information about the patient's status within a time course of the clinical condition can be obtained.

20. The method of claim 19, wherein the information is severity of the clinical condition.

21. The method of claim 19, wherein the clinical condition is ACS, and wherein the information is an estimated time of onset or severity of acute myocardial infarction or unstable angina.

22. A method for diagnosis of an acute coronary syndrome (ACS) or for risk stratification of a patient with suspected ACS, comprising the steps of:
a) obtaining at least one blood fraction sample from the patient;
b) conducting at least one in vitro diagnostic assay for albumin that has been modified by exposure to ischemic tissue and at least one in vitro diagnostic assay for a marker of necrosis on the sample;
c) measuring and analyzing the patient's electrocardiogram (ECG); and
d) combining the results of the assay(s) of step (b) and the ECG in step (c) using an algorithm to provide a positive or negative diagnosis of ACS or indication of the risk that the patient has ACS.

23. The method of claim 22, wherein the diagnosis of ACS includes at least one diagnosis selected from the group consisting of acute myocardial infarction, unstable angina, stable angina and cardiac ischemia.

24. The method of claim 22, wherein the marker for necrosis is selected from the group consisting of troponin, CK-MB and myoglobin.

25. The method of claim 22, wherein the diagnostic assay for modified albumin is selected from the group consisting of albumin cobalt binding (ACB®) test, an electrochemical test for ischemia modified albumin, an optical test for ischemia modified albumin, an immunoassay for ischemia modified albumin, and metal affinity assay for ischemia modified albumin.

26. The method of claim 22, wherein the algorithm provides a negative diagnosis or indication of lower risk of ACS if the ECG is either non-diagnostic or normal, and results of the assay for a marker of necrosis and the assay for the modified albumin are negative.

27. The method of claim 22, wherein the algorithm provides a positive diagnosis or indication of higher risk if the ECG is normal or non-diagnostic and at least one of the in vitro diagnostic assays for modified albumin and the in vitro diagnostic assays for a marker of necrosis is positive.

28. The method of claim 22, wherein the algorithm provides for a positive diagnosis or indication of higher risk if the ECG is non-diagnostic or normal, the in vitro assay for a marker of necrosis is negative and the in vitro assay for modified albumin is positive.

29. The method of claim 22, wherein the algorithm provides a positive diagnosis or indication of higher risk if the ECG is positive and at least one of the in vitro assays is positive.

30. The method of claim 22, further comprising repetition of steps (a) and (b) and/or repetition of step (c), followed by repetition of step (d), whereby information about a patient's status within a time course of the ACS can be obtained.

31. The method of claim 30, wherein the information is the onset of the occurrence of the ACS.

32. The method of claim 30, wherein the information is the severity of the ACS.

33. An apparatus for diagnosis of a clinical condition or estimating the probability of the presence of the condition in a patient, comprising:
an electronic module housing comprising a display means; a data entry and control means; a means for measuring an electrocardiogram (ECG); an aperture containing a reader means; an analysis means in electrical continuity with the data entry and control means, the ECG means, and the reader means, whereby said analysis means can analyze signals from each said means; a power source; and optionally a link to a laboratory or hospital information system;
wherein said aperture is adapted to receive a sample analysis strip for conducting an in vitro diagnostic assay on a patient sample of a substance stream, and said reader is adapted to read results of said assay;
whereby said analyzer receives signals from said ECG means and said data entry and control means, and upon insertion of said strip into said aperture, from said reader means, and said analyzer means transmits analyzed results to said display means.

34. The apparatus of claim 33, wherein the reader means comprises at least one reader device capable of reading results of an assay for a marker of ischemia, and/or assay results of an assay for a marker of necrosis on the sample analysis strip.

35. The apparatus of claim 33, wherein said link to a laboratory or hospital information system is selected from the group consisting of a direct electrical connection, an infrared link and a wireless link.

* * * * *

UNITED STATES PATENT AND TRADEMARK OFFICE
CERTIFICATE OF CORRECTION

PATENT NO.         : 7,074,194 B2                                                Page 1 of 1
APPLICATION NO. : 10/441155
DATED              : July 11, 2006
INVENTOR(S)        : Crosby et al.

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 241 days Delete the phrase "by 241 days" and insert -- by 361 days--

Signed and Sealed this

Twenty-sixth Day of June, 2007

JON W. DUDAS
*Director of the United States Patent and Trademark Office*